United States Patent
Babb et al.

(10) Patent No.: US 11,530,277 B2
(45) Date of Patent: *Dec. 20, 2022

(54) COMPOSITIONS AND METHODS FOR MAKING ANTIBODIES BASED ON USE OF AN EXPRESSION-ENHANCING LOCUS

(71) Applicant: REGENERON PHARMACEUTICALS, INC., Tarrytown, NY (US)

(72) Inventors: Robert Babb, River Edge, NJ (US); Darya Burakov, Tarrytown, NY (US); Gang Chen, Yorktown Heights, NY (US); James P. Fandl, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 830 days.

This patent is subject to a terminal disclaimer.

(21) Appl. No.: 16/095,067

(22) PCT Filed: Apr. 20, 2017

(86) PCT No.: PCT/US2017/028552
§ 371 (c)(1),
(2) Date: Oct. 19, 2018

(87) PCT Pub. No.: WO2017/184831
PCT Pub. Date: Oct. 26, 2017

(65) Prior Publication Data
US 2019/0263937 A1    Aug. 29, 2019

Related U.S. Application Data

(60) Provisional application No. 62/325,385, filed on Apr. 20, 2016.

(51) Int. Cl.
| | |
|---|---|
| C12N 9/22 | (2006.01) |
| C07K 16/46 | (2006.01) |
| C12N 15/85 | (2006.01) |
| C12N 15/90 | (2006.01) |
| C12Q 1/6897 | (2018.01) |
| C07K 16/00 | (2006.01) |

(52) U.S. Cl.
CPC ............ *C07K 16/468* (2013.01); *C07K 16/00* (2013.01); *C12N 15/85* (2013.01); *C12N 15/902* (2013.01); *C12Q 1/6897* (2013.01); *C07K 2317/51* (2013.01); *C07K 2317/515* (2013.01); *C07K 2317/526* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,634,665 A | 1/1987 | Axel et al. | |
| 4,656,134 A | 4/1987 | Ringold | |
| 6,800,457 B2 | 10/2004 | Koduri et al. | |
| 7,183,076 B2 | 2/2007 | Arathoon et al. | |
| 8,389,239 B2 | 3/2013 | Chen et al. | |
| 8,586,713 B2 | 11/2013 | Davis et al. | |
| 2010/0105042 A1 | 4/2010 | Taylor et al. | |
| 2013/0004946 A1 | 1/2013 | Chesnut et al. | |
| 2014/0088295 A1 | 3/2014 | Smith et al. | |
| 2014/0134719 A1 | 5/2014 | Deshpande et al. | |
| 2014/0179547 A1 | 6/2014 | Fischer et al. | |
| 2014/0308285 A1 | 10/2014 | Yan et al. | |
| 2015/0167020 A1 | 6/2015 | Rance et al. | |
| 2015/0218276 A1 | 8/2015 | Chen et al. | |
| 2015/0266966 A1 | 9/2015 | Smith et al. | |
| 2016/0115502 A1 | 4/2016 | Shen et al. | |

FOREIGN PATENT DOCUMENTS

| | | |
|---|---|---|
| CN | 104955844 A | 9/2015 |
| EP | 1 870 459 A1 | 12/2007 |
| JP | 2009-539349 A | 11/2009 |
| JP | 2012-531439 A | 12/2012 |
| WO | 03/101189 A1 | 12/2003 |
| WO | 2004/046340 A2 | 6/2004 |
| WO | 2007/110205 A2 | 10/2007 |
| WO | 2007/143168 A2 | 12/2007 |
| WO | 2008/119353 A1 | 10/2008 |
| WO | 2008/151219 A1 | 12/2008 |
| WO | 2009/089004 A1 | 7/2009 |
| WO | 2010/141478 A1 | 12/2010 |
| WO | 2010/151792 A1 | 12/2010 |
| WO | 2011/034605 A2 | 3/2011 |
| WO | 2011/131746 A2 | 10/2011 |
| WO | 2013/181253 A1 | 12/2013 |

(Continued)

OTHER PUBLICATIONS

Japanese Notice of Reasons for Rejection dated Apr. 12, 2021 received in Japanese Patent Application No. 2018-552822, together with an English-language translation.

(Continued)

*Primary Examiner* — Michael D Burkhart
(74) *Attorney, Agent, or Firm* — Scully, Scott, Murphy & Presser, P.C.; Todd R. Samelman

(57) ABSTRACT

This invention relates to site-specific integration and expression of recombinant proteins in eukaryotic cells. In particular, the invention includes compositions and methods for improved expression of antibodies including bispecifc antibodies in eukaryotic cells, particularly Chinese hamster (*Cricetulus griseus*) cell lines, by employing an expression-enhancing locus.

41 Claims, 5 Drawing Sheets

Specification includes a Sequence Listing.

(56) References Cited

FOREIGN PATENT DOCUMENTS

| WO | 2013/190032 A1 | 12/2013 |
| WO | 2014/121087 A1 | 8/2014 |
| WO | 2016/064999 A1 | 4/2016 |
| WO | 2017053856 A1 | 3/2017 |

OTHER PUBLICATIONS

Araki K. et al., "Site-Directed Integration of the Cre Gene Mediated by Cre Recombinase Using a Combination of Mutant Lox Sites", Nucleic Acids Research 30(19):e103 (2002).

Baser B. et al., "A Method for Specifically Targeting Two Independent Genomic Integration Sites for Co-Expression of Genes in CHO Cells", Methods 95:3-12 (2016), together with Supplementary Materials.

Boch J. et al., "Breaking the Code of DNA Binding Specificity of TAL-Type III Effectors", Science 326:1509-1512 (Dec. 11, 2009).

Chen H. et al., "Cut Site Selection by the Two Nuclease Domains of the Cas9 RNA-Guided Endonuclease", The Journal of Biological Chemistry 289(19):13284-13294 (May 9, 2014).

Crawford Y. et al., "Fast Identification of Reliable Hosts for Targeted Cell Line Development from a Limited-Genome Screening Using Combined C31 Integrase and CRE-Lox Technologies", Biotechnol. Prog. 29(5):1307-1315 (2013).

Doerner A. et al., "Therapeutic Antibody Engineering by High Efficiency Cell Screening", FEBS Letters 588:278-287 (2014).

Frenzel A. et al., "Expression of Recombinant Antibodies", Frontiers in Immunology 4(217):1-20 (Jul. 2013).

Kawabe Y. et al., "Repeated Integration of Antibody Genes into a Pre-Selected Chromosomal Locus of CHO Cells Using an Accumulative Site-Specific Gene Integration System", Cytotechnology 64:267-279 (2012).

Kim S.K. et al., "Stable Reduction of Thymidine Kinase Activity in Cells Expressing High Levels of Anti-Sense RNA", 42:129-138 (Aug. 1985).

Klar M. et al., "Dominant Genomic Structures: Detection and Potential Signal Functions in the Interferon-Beta Domain", Gene 364:79-89 (2005).

Kontermann R.E. et al., "Bispecific Antibodies", Drug Discovery Today 20(7):838-847 (Jul. 2015).

Kostelny S.A. et al., "Formation of a Bispecific Antibody by the Use of Leucine Zippers", The Journal of Immunology 148(5):1547-1553 (Mar. 1, 1992).

Kriz A. et al., "A Plasmid-Based Multigene Expression System for Mammalian Cells", Nature Communications 1:120:DOI:10.1038 (2010).

Lai T. et al., "Advances in Mammalian Cell Line Development Technologies for Recombinant Protein Production", Pharmaceuticals 6:579-603 (2013).

Lattenmayer C. et al., "Identification of Transgene Integration Loci of Different Highly Expressing Recombinant CHO Cell Lines by FISH", Cytotechnology 51(3):171-182 (Nov. 15, 2006).

Li J. et al., "Analysis of IgG Heavy Chain to Light Chain Ratio With Mutant Encephalomyocarditis Virus Internal Ribosome Entry Site", Protein Engineering, Design & Selection 20(10):491-496 (2007).

Qiao J. et al., "Novel Tag-and-Exchange (RMCE) Strategies Generate Master Cell Clones With Predictable and Stable Transgene Expression Properties", J. Mol. Biol. 390:579-594 (2009).

Racher A., "Establishment of Cell Lines for Manufacturing Recombinant Antibodies", 2004, Lonza Presentation.

Szymczak A L et al., "Development of 2A Peptide-Based Strategies in the Design of Multicistronic Vectors", Expert Opinion Biol. Ther. 5(5):627-638 (2005).

Turan S. et al., "Recombinase-Mediated Cassette Exchange (RMCE)—A Rapidly-Expanding Toolbox for Targeted Genomic Modifications", Gene 515(1):1-27 (Feb. 1, 2013).

Turan S. et al., "Site-Specific Recombinases: From Tag-and-Target to Tag-and-Exchange-Based Genomic Modifications", The FASEB Journal 25:4088-4107 (2011).

Turan S. et al., "Multiplexing RMCE: Versatile Extensions of the Flp-Recombinase-Mediated Cassette-Exchange Technology", J. Mol. Biol. 402:52-69 (2010).

Wiberg F.C. et al., "Production of Target-Specific Recombinant Human Polyclonal Antibodies in Mammalian Cells", Biotechnology and Bioengineering 94(2):396-405 (Jun. 5, 2006).

Wilke S. et al., "Streamlining Homogeneous Glycoprotein Production for Biophysical and Structural Applications by Targeted Cell Line Development", PLoS One 6(12):e27829 (Dec. 2011).

Zboray K. et al., "Heterologous Protein Production Using Euchromatin-Containing Expression Vectors in Mammalian Cells", Nucleic Acids Research 43(16):e102 (Sep. 18, 2015).

Zhang L. et al., "Recombinase-Mediated Cassette Exchange (RMCE) for Monoclonal Antibody Expression in the Commercially Relevant CHOK1SV Cell Line", Biotechnology Progress 31(6):1645-1656 (Oct. 13, 2015).

Zhou C. et al., "Development of a Novel Mammalian Cell Surface Antibody Display Platform", mABS 2(5):508-518 (Sep./Oct. 2010).

International Search Report dated Jul. 13, 2017 received in International Application No. PCT/US2017/028552.

Chinese Office Action dated Oct. 11, 2021 received in Chinese Patent Application No. 201780024560.2, together with an English-language translation.

Bispecific antibody-producing cell line

Bispecific antibody-producing cell line

Bispecific antibody-producing cell line

SEQUENCE LISTING

<160> NUMBER OF SEQ ID NOS: 3

<210> SEQ ID NO 1
<211> LENGTH: 13515
<212> TYPE: DNA
<213> ORGANISM: Cricetulus griseus

<400> SEQUENCE: 1

```
tctagaaaca aaaccaaaaa tattaagtca ggcttggctt caggtgctgg ggtggagtgc      60
tgacaaaaat acacaaattc ctggctttct aaggcttttt cggggattca ggtattgggt     120
gatggtagaa taaaatctg aaacataggt gatgtatctg ccatactgca tgggtgtgta     180
tgtgtgtgta tgtgtgtctg tgtgtgtgcc cagacagaaa taccatgaag gaaaaaaaca     240
cttcaaagac aggagagaag agtgacctgg gaaggactcc ccaatgagat gagaactgag     300
cacatgccag aggaggtgag gactgaacca ttcaacacaa gtggtgaata gtcctgcaga     360
cacagagagg gccagaagca ctcagaactc caggggggtca ggagtggttc tctggaggct     420
tctgcccttg gaggttcctg aggaggaggc ttccatattg aaaatgtagt tagtggccgt     480
ttccattagt acagtgacta gagagagctg agggaccact ggactgaggc ctagatgctc     540
agtcagatgg ccatgaaagc ctagacaagc acttccgggt ggaaaggaaa cagcaggtgt     600
gaggggtcag gggcaagtta gtgggagagg tcttccagat gaagtagcag gaacggagac     660
gcactggatg gccccacttg tcaaccagca aaagcttgga tcttgttcta agaggccagg     720
gacatgacaa gggtgatctc ggttttttaaa aggctttgtg ttacctaatc acttctatta     780
gtcagatact ttgtaacaca aatgagtact tggcctgtat tttagaaact ctgggatcc     840
tgaaaaaaca caatgacatt ctggctgcaa cacctggaga ctcccagcca ggccctggac     900
ccgggtccat tcatgcaaat actcagggac agattcttca ctaggtactg atgagctgtc     960
ttggatgcaa atgtggcctc ttcattttac tacaagtcac catgagtcag gaggtgctgt    1020
ttgcacagtg tgactaagtg atggagtgtt gactgcagcc attcccggcc ccagcttgtg    1080
agagagatcc ttttaaattg aaagtaagct caaagttacc acgaagccac acatgtataa    1140
actgtgtgaa taatctgtgc acatacacaa accatgtgaa taatctgtgt acatgtataa    1200
actgtgtgaa taatctgtgt gcagcctttc cttacctact accttccagt gatcaggttt    1260
ggactgcctg tgtgctactg gaccctgaat gtccccaccg ctgtcccctg tcttttacga    1320
ttctgacatt tttaataaat tcagcggctt ccctctgct ctgtgcctag ctataccttg    1380
gtactctgca ttttggttc tgtgacattt ctctgtgact ctgctacatt ctcagatgac    1440
atgtgacaca gaaggtgttc cctctggaga catgtgatgt ccctgtcatt agtggaatca    1500
gatgccccca aactgttgtc cagtgtttgg gaaagtgaca cgtgaaggag gatcaggaaa    1560
agaggggtgg aaatcaagat gtgtctgagt atctcatgtc cctgagtggt ccaggctgct    1620
gacttcactc ccccaagtga gggaggcat ggtgagtaca cacacctcac acatactata    1680
tccaacacac acacacacac acacacacac acgcacgcac gcacgcacgc acgcacacat    1740
gcacacacac gaactacatt tcacaaacca catacgcata ttacaccca aacgtatcac    1800
```

```
ctatacatac cacacataca cacccctcca cacatcacac ataccacca cccacacaca    1860 gcacacacat acataggcac acattcacac accacacata tacatttgtg tatgcataca    1920
tgcatacaca cacaggcaca cagacaccac acacatgcat tgtgtacgca cacatgcata    1980
cacacacata ggcacacatt gagcacacac atacatttgt gtacgcacac tacatagaca    2040
tatatgcatt tgtatatgca cacatgcatg cacacataca taggcacaca tagagcacac    2100
acatacattt gtgtatgcac acatgcacac accaatcaca tgggaagact caggttcttc    2160
actaaggttc acatgaactt agcagttcct ggttatctcg tgaaacttgg aagattgctg    2220
tggagaagag gaagcgttgg cttgagccct ggcagcaatt aaccccgccc agaagaagta    2280
ggtttaaaaa tgagagggtc tcaatgtgga acccgcaggg cgccagttca gagaagagac    2340
ctacccaagc caactgagag caaaggcaga gggatgaacc tgggatgtag tttgaacctc    2400
tgtaccagct gggcttcatg ctatttgtt atatctttat taaatattct tttagtttta    2460
tgtgcgtgaa taccttgctt gcataaatgt atgggcactg tatgtgttct tggtgccggt    2520
ggaggccagg agagggcatg gatcctccgg agctggcgtt tgagacagtt gtgacccaca    2580
gtgtggggtc tgggaactgg gtcttagtgt tccgcaagtg cagctgggc tcttaacctc    2640 tgagccatcc ctccagcttc aagaaactta ttttcttagg acatggggga agggatccag    2700
ggctttaggc ttgtttgttc agcaaatact cttttcgtgt attttgaatt ttattttatt    2760 ttacttttt gggatagaat cacattctgc agctcaggct gggcctgaac tcatcaaaat    2820
cctcctgtct cagtctacca ggtgataaga ttactgatgt gagcctggct ttgacaagca    2880
ctttagagtc cccagcccctt ctggacactt gttccaagta taatatatat atatatatat    2940
atatatatat atatatatat atatattgtg tgtgtgtgtt tgtgtgtgta tgagacactt    3000
gctctaaggg tatcatatat atccttgatt tgcttttaat ttatttttta attaaaaatg    3060
attagctaca tgtcacctgt atgcgtctgt atcatctata tatccttcct tccttctctc    3120
tctttctctc ttcttcttct cacccccaag catctatttt caaatccttg tgccgaggag    3180
atgccaagag tctcgttggg ggagatggtg aggggggcgat acaggggaag agcaggagga    3240 aaggggggaca gactggtgtg ggtctttgga gagctcagga gaatagcagc gatcttccct    3300
gtccctggtg tcacctctta cagccaacac cattttgtgg cctggcagaa gagttgtcaa    3360
gctggtcgca ggtctgccac acaaccccaa tctggcccca agaaaaggca cctgtgtgtg    3420
actctggggt taaaggcgct gcctggtcgt ctccagctgg acttgaaact cccgtttaat    3480
aaagagttct gcaaataat acccgcagag tcacagtgcc aggttcccgt gctttcctga    3540
agcgccaggc acgggttccc taggaaatgg ggccttgctt gccaagctcc cacggcttgc    3600
cctgcaaacg gcctgaatga tctggcactc tgcgttgcca ctgggatgaa atggaaaaaa    3660
gaaaaagaag aagtgtctct ggaagcgggc gcgctcacac aaacccgcaa cgattgtgta    3720
aacactctcc attgagaatc tggagtgcgg ttgccctcta ctggggagct gaagacagct    3780
agtgggggcg gggggaggac cgtgctagca tccttccacg gtgctcgctg gctgtggtgc    3840
atgccgggaa ccgaaacgcg gaactaaagt caagtcttgc tttggtggaa ctgacaatca    3900
acgaaatcac ttcgattgtt ttcctctttt tactggaatt cttggatttg atagatgggg    3960
gaggatcaga gggggagggg aggggcgggg agacggaggg aggaggggag gagggagga    4020 gggagggag ggaggaggg aagggatgga ggaaaatact aacttttcta attcaacatg    4080
acaaagattc ggagaaagtg caccgctagt gaccgggagg aggaatgccc tattgggcat    4140
```

```
tatattccct gtcgtctaat ggaatcaaac tcttggttcc agcaccaagg attctgagcc    4200
tatcctattc aagacagtaa ctacagccca cacggaagag gctatacaac tgaagaaata    4260
aaattttcac tttatttcat ttctgtgact gcatgttcac atgtagagag ccacctgtgt    4320
ctaggggctg atgtgctggg cagtagagtt ctgagcccgt taactggaac aacccagaac    4380
tcccaccaca gttagagctt gctgagagag ggaggcccct ggtgagattt ctttgtgtat    4440
ttatttagag acagggtctc atactgtagt ccaagctagc ctccagctca cagaaattct    4500
cctgttccgg tttccaaagt actggagtta tgagtgtgtg ttaattgaac gctaagaatt    4560
tgctgattga agaaaacctc aagtgggttt ggctaatccc cacgacccca gaggctgagg    4620
caggaggaat gagagaattc aaggtttgcc agagccacag ggtgagctca atgtggagac    4680
tgtgagggtg agctcaatgt ggagactgtg agggtgagct caatgtggag actgtgaggg    4740
tgagctcaat gtggagactg tgagggtgag ctcaatgtgg agactgtgag ggtgagctca    4800
atgtggagac ctgtatcaag ataataatag tagtagtaac aatgcaggcg agggtgtggt    4860
tgagtggtag agcagttagt tgatttgaca tgcttgaggt ctcccggtcc atctgtggcc    4920
ctgcaacagg aagggaggga ggaaggggggg gaacgagaga gaggaaagag agacagaagc    4980
taagataggg aatgagagag gaaggaagaa acgggaagaa attcagactc cttcctgagt    5040
tccgccaacg cctagtgaca tcctgtgcac accctaaggt ggcctttgtg tggcactggc    5100
ttgggtggtc gggaaaggca ttttcagctt gttgcagaac tgccacagta gcatgctggg    5160
tccgtgaaag tttctgcccg ttaacaagaa gtctctacta cttgtgacct caccagtgaa    5220 aatttctta attgtctcct ggtgttctgg gttttgcatt tttgtttcta aggatacatt    5280
cctgggtgat gtcatgaagt ccccaaagac acagtggggc tgtgttggat tgggaaagat    5340
gatttatctg gggtgtcaaa aggaaaagaa gggaaacagg cacttgggaa aatgtcctcc    5400
cgcccacccg aatttttggct tggcaaccgt ggtggaggag caagaaacac gtggacgttt    5460
gaggaggcat ggggtcctag gaggacagga agcagaagga gagagctggg ctgacagcct    5520
gcaggcattg cacagtttca gaaggagatt acagcatgac tgagttttta gggatccaac    5580
agggacctgg gtagagattc tgtgggctct gaggcaactt gacctcagcc agatggtatt    5640
tgaataacct gctcttagag ggaaaacaga catagcaaac agagccacgt ttagtgatga    5700
aactctcact ttgcctgagt catgtgcggc catgcccagg ggtcaggctg acactcaact    5760
caaaaacaag tgagaaattg aagacaatcc gtggtggcag ctactggaag ggccaccaca    5820
tccccagaaa gagtggagct gctaaaaagc catttgtgat aggcacagtt atcttgaatg    5880
catggagcag agattacgga aaaatcgaga atgttaatga ggcaacattc gagttgagtc    5940
attcagtgtg ggaaacccag acgcttccat cccctaaaag gaacatcttg ctctcagtca    6000
aaatggaaat aaaaattggg gcttgaattt ggcaaatgat tcagaactct gtgtaggtat    6060
tttcacacgc acagtggata atttcatgt tggagtttat ttgtgctaaa aggcagaaaa    6120
gggtaaaaag cacatcttaa gagttatgag gttctacgaa taaaaataat gttacttaca    6180
gctattcctt aattagtacc cccttccacc tgtggtaatt tcctgagata gtcagtgggg    6240
aaaagatctc tccttctctt ctttctcccc ctccctcct ctccctccct cctcccctcc    6300
ctccctcctc tccctccctc ccctttcct tctttctttg ctccttctcc tctgcctcct    6360 tctcccttc ttcttcattt attctaagta gcttttaaca gcacaccaat tacctgtgta    6420
taacgggaaa acacaggctc aagcagctta gagaagattg atctgtgttc actagcgtgc    6480
aattcagagg tgggtgaaga taaaaggcaa acatttgagg ccatttcctt atttggcacg    6540
```

```
gcacttagga agtggaacat gcctaatcta ctggtttgta ccacctttcc ctataatgga    6600
ctgtttggga agctcctggg caaccgattc tggcatctca ttggtcagag gcctgttaaa    6660
tggtactctt atttgcaaag aaggctgtaa cttgtagctt taaaagcctc tcctcaagaa    6720
agaagggaga aaggatatgg ctagacatat ctaatagact taaccactgt gaaaagcctt    6780
agtatgaatc agatagaacc tattttaac tcagttttga aaaaaataat ctttatattt     6840
atttgtgtgt gtgtgtgtgt gtgtgtgtgt gtgtgtgtgt gtgtgtgtgt gaaccacatg    6900
tagcaggtgc tggaggaggc cagaagaggg caccagatct cctggaactg acaccacaca    6960
tggttatgag ctgcctgatg tgggtgctgg gaactgaact ctcgtgttct gcaagagcag    7020
caactgttct cttaactgat gagccatctc tccagccccc cccataattt taattgttca    7080
ttttagtaaa ttttattcat aatcaattat cacagtataa aacaatgatt ttatatatat    7140
catatacata tcaaggatga cagtgagggg gatatgtgtg tgtgtgtgtg tgtgtgtgtg    7200
tgtgtgtgtg tgtgttattt gtgtgtgtgc ttttaagaa ggtgccatag tcactgcatt     7260
tctctgaagg atttcaaagg aatgagacat gtctgtctgc caggaaccct atcttcctct    7320
ttgggaatct gacccaaatg aggtattctg aggaactgaa tgaagagctc aagtagcagt    7380
gtcttaaacc caaatgtgct gtctagagaa agtcaacgtc atcagtgagc tgaggagaga    7440
tttactgagc ggaagacaag cgctctttga tttaagtggc tcgaacagtc acggctgtgg    7500
agtggagcct gtgctcaggt ctgaggcagt ctttgctagc cagctgtgat gagcagtgaa    7560
gaaagggtgg agatggaggc agggtgggag cagggctatg gttcagacta ggtatcgtga    7620
gcacaccagc tggttgactt gtggtctgtg ggtcaggcgt tgtaaacgcc ctcagggtca    7680
ggcagtcaca ttgcttgaag ctgaatgggt gaggcaacac agagagtgca aagaaggcaa    7740
agtaccacct cttccccgac ccaggtcact tctgggttat agctgagact ccggacagca    7800
tgcaaccagc tggttagagc ttcagggaaa acttgatgtc tgcatgttgc tatgaaatgt    7860
gattcggtac atctggagaa aatttataat gctggctcag tcaagcactg aacaaaggta    7920
ccttggcttt gggagctaca tgacattgac ttgtaggcag acttttttt ttctgcccgc     7980 caattcccag ataaccaata tggaggctca atattaatta taaatgctcg gctgatagct    8040
caggcttgtt actagctaac tcttccaact taaatgaacc catttctatt atctacattc    8100
tgccacgtga ctttaccttg tacttcctgt ttcctctcct tgtctgactc tgcccttctg    8160
cttcccagag tccttagtct ggttctcctg cctaacctta tcctgcccag ctgctgacca    8220
agcatttata attaatatta agtctcccag tgagactctc atccagggag gacttgggtg    8280 ctccccctc ctcattgcca tccgtgtctt cctcttccct cgcttccccc tcctcttcct    8340
gctcttcctc ctccacccct cctttcatag tattgatggc aagggtgttc tagaatggag    8400
gagtgcccat aggcatgcaa agaaaccagt taggatgctc tgtgaggggt tgtaatcata    8460
agcgatggac acaattcaag ccacagagtg aagacggaag gatgcactgt gctctagagc    8520
aacttctggg gcagaatcac agggtgagtt tctgacttga gggcgaagag gccacgagga    8580
agggagtgag tttgtctgag ctagaagcta cggcccacct cttggtagca gacctgccca    8640
caagcatgct ttgttaatca tgtgggatct gattttcctc taaatctatg ttcaactctt    8700
aagaaaatgt gaattctcac attaaaattt agatatacgt cttttggtgg ggggggtgta    8760
aaaaatcctc aagaatatgg atttctgggg gccggagaga tggctcagag gttaagagaa    8820
ctggttgctc ttctagacat tctgagttca attcccagca accacatggt ggctcacaac    8880
```

-continued

```
catctgtaat gcgacctggt gccatcttct gacatgcatg gatacatgca ggcagaaagc    8940
tgtatacata gtaaattgat aaatcttttt ttaaaaagag tatggattct gccgggtgtt    9000
ggtggcgcac gcctttaatc ccagcactct ggaggcagag gcaggtggat ctctgtgagt    9060
tcgagaccag cctggtctat aagagctagt tccaggacaa cctccaaagc cacagagaaa    9120
ccctgtctcg aaaaccaaa aaaaaaaaaa aaaaaaaaa aaaaaaaga gtatggattc       9180 taagaaagcc gtaacagctg gagctgtgta cggagttcag cgtggtacta aagaacaga    9240 cattcatgat gaaacacccc aggatttta cttagtatct agtttccatt gttgttttga   9300
gaccggctct tatgctctcc aggctggcct caaactgctg atcttcccgc ctctacctct   9360
caagtcctgg gactacttgg ctcataaaac agttttttgtc gggctccctg aagttatggt  9420
tgtacaaacc gtgggggtca atatactcac ttgggcagag agagaaggtc tgaatcccag   9480
acaatgactg catctcagga cagttgggaa gaggacaatg gcagaaggac ttagaaaaga   9540
tagactggag ggtggaaaag cagcaggaac agagaaacaa aacaggaagc ttgctatcca   9600
gggccactct ggagtcctgt ggcaagatgg aagcgggcta ggggaataca tttgtgctac   9660
tgtgtgtgtg tgtgtgtgtg tgtgtgtgtg tgtgtgtgat caatgcctat caatgttgaa   9720
ggggaaatat gtataccaca ttgattctgg gagcaattct cagtatctgg cctagagaaa   9780
ggaatggccc ctgcagaata gacagagtga atggtgccct ttatcatttg ctaaagtgaa   9840
ggagaaataa acatccttcc atagagtttc aggtaaatga accccacagt tcatctgtgc   9900
cgtggtggag gcctggccaa cagttaaaaa gattagacac ggacaaagtc tgaaggaaac   9960
acctcgaata ggaagaggag agccacctca ttctgtaact ttcctcaagg ggaagatgtt   10020
ccaagagtgg gaataaatgg tcaaggggg gattttttaat taggaaaacg atttcctgta   10080
tcacttgtga aactggaggt tgatttgggg cataggacaa tagatttgat gctttgcaaa   10140
aagctgtttc aaagcagaga atggaatag agacaattat gtagcgagga gggagggtgg    10200
ggcgaagatg gagacagaga agtggaagct gactttaggg aagaggaaca tagaccacag   10260
gggcggggcg gggggcaggg gcgggggggcg gggctcaaag gaggcagtgg gaacgttgct   10320
agtgttcgca gcgtaagcgt gaatgtgcaa gcgtctttgt ggtgtgtgac caggagtagc   10380
gtggctggct tgtgtgctgc ttgtaatccc agtctttgag gtttccacac tgttccacag   10440
tgggtgtgat tttccctcgg agagcatgag ggctctgctt tccccacatc ctccccagcg   10500
ttcgttggta tttgtttcca agatgttagt gggtgagaca aagcctctct gttgatttgc   10560
ctttaacagg tgacaaaaaa agctcaacca ggagacattt ttgccttctt ggaaggtaat   10620
gctcccatgt agagcaatgg gacccatctc taaggtgagg ctactcttgc agtttgcacc   10680
cagctcttct gatgcaggaa ggaagttggt gggcaagcaa gactgtttgc ttcttgcgat   10740
ggacacattc tgcacacaaa ggctcaggag gggagaaggc tgtttgatgt ttagcactca   10800
ggaaggcccc tgatgcatct gtgattagct gtctccatct gtggagcaga cacggactaa   10860
ctaaaaacca gtgttttaa attgtcaagc ctttaaggtg aggaaattga cttattgtgc   10920
tgggccatac gtagagcaag tgctctgcat tgggccaacc cccggctctg gtttctaggc   10980
accagaatgg cctagaacta actcacaatc ctcccattcc aggtctcagg tgctagaatg   11040
aaccactata ccagcctgcc tgcctgccta cctgccttcc taaatttaa atcatgggga    11100 gtagggagaa atacacttat cttagttagg gtttctattg ctgtgaagag acaccatgag   11160
catggcaact cttataaagg aaaacattta gttgggtggc agtttcagag gttttagtac   11220
attgtcatca tggctgggaa catgatggca tgcagacaga catggtgctg gagaaaggga   11280
```

```
tgagagtcct acatcttgca ggcaacagga cctcagctga gacactggct ggtaccctga   11340
gcataggaaa cctcacagcc caccctcaca gtgacatatt tccttcaaca aagccatacc   11400
tcctaatagt gccactccct atgagatgac agggccaatt acattcaaac tgctataaca   11460 cttttaaagta ttttatttttt attattgtaa attatgtatg tagctgggtg gtggcagccg   11520
aggtgcacgc ctttaatccc agcacttggg aggcagaggc agatggatct ctgtgagttc   11580
aagaccagcc tggtctataa gagctagttg caaggaagga tatacaaaga acagttctag   11640
gatagccttc aaagccacag agaagtgctg tcttgaaaac caaaaattgt gctgggacct   11700
gtctctgctt tggttgcttc ccactccccc agagctggac tcttggtcaa cactgaatca   11760
gctgcaaaat aaactcctgg attcctctct tgtaacagga gcccgaagtc aggcgcccac   11820
ttgtcttctc gcaggattgc catagacttt ttctgtgtgc ccaccattcc agactgaagt   11880
agagatggca gtggcagaga ctgggaaggc tgcaacgaaa acaggaagtt attgcaccct   11940
gggaatagtc tggaaatgaa gcttcaaaac ttgcttcatg ttcagttgta cacagactca   12000
ctcccaggtt gactcacacg tgtaaatatt cctgactatg tctgcactgc ttttatctga   12060
tgcttccttc ccaaaatgcc aagtgtacaa ggtgagggaa tcacccttgg attcagagcc   12120
cagggtcgtc ctccttaacc tggacttgtc tttctccggc agcctctgac acccctcccc   12180
ccattttctc tatcagaagg tctgagcaga gttggggcac gctcatgtcc tgatacactc   12240
cttgtcttcc tgaagatcta acttctgacc cagaaagatg gctaaggtgg tgaagtgttt   12300
gacatgaaga cttggtctta agaactggag caggggaaaa aagtcggatg tggcagcatg   12360
tacccgaaat cccagaactg ggagggtaga gacggatgag tgcccggggc tagctggctg   12420
ctcagccagc ctagctgaat tgccaaattc caactcctat tgaaaaacct ttaccaaaca   12480
aacaaacaaa caaataataa caacaacaac aacaacaaac taccccatac aaggtgggcg   12540
gctcttggct cttgaggaat gactcaccca aacccaaagc ttgccacagc tgttctctgg   12600
cctaaatggg gtgggggtgg ggcagagaca gagacagaga gagacatgac ttcctgggct   12660
gggctgtgtg ctctaggcca ccaggaactt tcctgtcttg ctctctgtct ggcacagcca   12720
gagcaccagc acccagcagg tgcacacacc tccctccgtg cttcttgagc aaacacaggt   12780
gccttggtct gtctattgaa ccggagtaag ttcttgcaga tgtatgcatg gaaacaacat   12840
tgtcctggtt ttatttctac tgttgtgata aaaccggggg aactccagga agcagctgag   12900
gcagaggcaa atgcaaggaa tgctgcctcc tagcttgctc cccatggctt gccgggcctg   12960 cttttctgcaa gcccttctct ccccattggc atgcctgaca tgaacagcgt ttgaaatgct   13020
ctcaaatgtc actttcaaag aaggcttctc tgatcttgct aactaaatca gaccatgttt   13080
caccgtgcat tatctttctg ctgtctgtct gtctgtctgt ctgtctatct gtctatcatc   13140
tatcaatcat ctatctatct atcttctatt tatctaccta tcattcaatc atctatcttc   13200
taactagtta tcatttattt atttgtttac ttactttttt tatttgagac agtatttctc   13260
tgagtgacag ccttggctgt cctggaaccc attctgtaac caggctgtcc tcaaactcac   13320
agagatccaa ctgcctctgc ctctctggtg ctggggttaa agacgtgcac caccaacgcc   13380
ccgctctatc atctatttat gtacttatta ttcagtcatt atctatcctc taactatcca   13440
tcatctgtct atccatcatc tatctatcta tctatctatc tatctatcta tctatcatcc   13500
atctataatc aattg                                                     13515
```

<210> SEQ ID NO 2

```
<211> LENGTH: 14931
<212> TYPE: DNA
<213> ORGANISM: Cricetulus griseus
<220> FEATURE:
<221> NAME/KEY: misc_feature
<222> LOCATION: (2176)..(2239)
<223> OTHER INFORMATION: n is a, c, g, t or nucleotide is missing

<400> SEQUENCE: 2
catgtacact tatgcaagta tgatatggcc caacacagta ttttacacca attttatct        60 ataaaatata catgtacatc aaaatatatt attaataata acatcattat tctttctttc      120
caagtaataa acacatacac tgaaattttg gttcttgtgg ataatttaa tgaaacagga       180 aatgcaaatt tatcttagca tgtttacttc actttctttg catagataac cagtaatcac      240
attgatggat catgtagtga aatgtatttt taggtatcta aggaattttg gcttcgtttt      300
gtgcttgttg acactgaatt ctattcctaa caacagtgtg taaggattct gtctgattc       360 ttttaccagt atttgtccat ttgcatttc tttattattc atggctgctg ttctagaaag       420
tggaaggtag tgtgtcaagt ctgtttaaca tgtttccctg atgatcagtg tcttaacacc      480
tctctgagta catgttggcc aatgtcgttt ctagacccat ctattcttgc ttgacttatc      540
ctggtacatg cctgccaaga aatttctcct catcctttct gtctcttcac tgatttactt      600
gatgtgtgga tttcacattg atcatatgga aatagaagat acaatttct ttattcacag       660 tttggaagac tttcaatctc atagatcatc attattttt gctactgttc cctatgctat       720
ggtgaaattt ccatttgaat aattgcttaa acaattaaca agaaagaatc tattttact       780 tgcaataact tccatttcag aacatttact acactgttac tatatccaaa aactagtttt      840
atatatcatg tgagaaatga ctaattcata atttggccat gacattttt tcagaaacag       900 aaaaagtgac caatacatac acaatgctat aaatattaag acttcagcaa attaaatatt      960
tattcatgat atcacataaa attcatttat tatgtttat ttaaatgtgt ttttaaaaca      1020
gtggtatcac taaatattaa gttagatgtg tttatgtgct taatgaattt atattttaga     1080
atgttataag ttgtatatag tcaaatatgt aataaatttt atttttagg tctttctcat      1140 taaggtatt taattttggg tcccttttcc agagtgactc tagctcatga tgagttgaca      1200
taaaaactaa acagtacaaa atgtacattg cattcagtat tgcacttgat ctttgcactg     1260
aagtttgagt cagttcatac atttagtact tgggaagtac attaagctaa ctttcattgc     1320
tctggcaaaa tgctcgataa gataagagtc tattgtggaa agccatggca gcaggaaagt     1380
aagactgctg atgatgttta atccatagtc aagacgcaga aggagatgaa tgctggtatc     1440 caacatttt tgctgttcat tttctctaga accctagtcc ataaagatgt atgacttgca     1500
ttcaaaatgc gtccccttca gttgttcaac ttttctgtaa atatcctttc aggcatgtct     1560
agaagattgt ttcgcaaata cttctcaatc cattcaagtt gatagtgcag attaatcact     1620
gcagaataaa agcctgtaac ttggctcacg tgccaaggaa tatgcacact cctgacacat     1680
caataagtaa atcaaagtgt agcttttgcc tttaacattg ccagacttat gtaatgttct     1740
gcacgttctt cctccatcac ttttattct aatggtgttt ccttgacatt gaatcacgct     1800
gtggaagctg cttagaatta acattgaaat ctactgatat atttatgatg cagcaattta     1860
gatttactat tttacttaga attttttata attgagagaa tataatattt tcacagttat     1920
ctatctgctg taaatagagg atttaaaaa aaatctctat aacttttttt tacaacacac      1980
agtaaaatta agttaaaatt taataaagtc actatgttga tttcaaagtg tgctacgccc     2040
acggtggtca cgcaggtgta gcagaagatg ccactaaggt gggctaaggc cgatgggttg     2100
```

```
gggtctgcgc tccctggaga tgagcccag gcggttccct ggcaatcagc tgcgatcatg    2160
atgcccgatg agccannnnn nnnnnnnnnn nnnnnnnnnn nnnnnnnnnn nnnnnnnnnn    2220
nnnnnnnnnn nnnnnnnnnc tgggtgactt tatggaaaga atttgataga tttcatgatg    2280
tagaagaatt ttattaggct tattttacag gagactaaga ccctgggacc taaagatatc    2340
tgggtcctga aatcaggaa atgggtagag acgtggttga tggtatgaga cagattttag    2400
agaactctta gatcatgggc aatgaccgca atctgatgct tagaatagat catctataaa    2460
caattatgct gttcttttc tttctgttgt atgatctgat gatgtagccc ccttgccaag    2520
ttccctgatc cccccttgcca agttccctga ttgtaacagt atataagcat tgcttgagag    2580
catattcaac tacattgagt gtgtctgtct gtcatttcct cgccgattcc tgatttctcc    2640
ttgagccttt tccctcgtgttc tccctcggtc ggtggtctcc acgagaggcg gtccgtggca    2700
aaagtgtata aatgttctaa aacatttgaa ctctaaaaca tgcaaaatga aaattaaaa    2760 taaataaaca tgaaaattaa aatatatag ctgctaaaag ttaaacaata ctatataata    2820
ttttgttatt agaattcaaa atcacattag ttggatttaa tttgaacatt gcattctttc    2880
aataataatt tcaataaaaa aagtttcccc atgatagtag aaaataataa catatgtatc    2940
tatctattta tttaactaca catatatagc atttgtttca actaaaataa atgaatgagc    3000
aaagcaccta agtaattggt gtctattata tttatgaagc caatagtttc aaataaatta    3060
tcatgcataa ggaggtattg caaatgttaa accttttttg aaacagatat tcccagttac    3120
agaaattata atttctaatc tttcctataa gtagaatgat gataattaat ataggccatt    3180
tgtaaataat gttcagatta aaatattctc tatttcacta gagaagaatg atattaaatg    3240
tattatattt tatttcccat tttgtttgca ccactattct atatccctca gcagtttaaa    3300
tttgtttcac catatgtgtg tgtgtttgta tcttaaatat ggcactaaaa ttagaataat    3360
ttaatataaa tctttaggag aaaagatatt gaattatttt atgttgatag gaaaatatct    3420
tttaattgtc caagaatact ttttcttcta ttttaggact gatcagaccc aggactaata    3480
ttttatatgt actaattcta tgtaccaaaa tatgttatta tctcatgaat tctgtctcaa    3540
tattgaggta ataaaaatag tccatcatga actttaaaat taaataatg attaattaat    3600 ttttattcat attttgtttg tatgaatggt tatacatcac atgtgtgcct ggtgactgtg    3660
aatgtcagga gaaggtatga aagccactgg aattggaata agagataata tttgagatgt    3720
tatgtgggtg ctgagaatta gacgcaagcc atcttcaaga atagccagca tactatacca    3780
ctgagtaatc cattcatccc tcaataatta tctttgtaga cagtaaatat atttctaaac    3840
tataaatgac cagaaaaatt aatgtattat taatgaagac attcatctca tgtgacacac    3900
ttcacctgtc taaatcagta acactctctc cactaattaa gattttctaa gtgcatgaca    3960
cttactattt ctaaagctgt ccaatggggg ccagtcccca gtcagcaccc agtgagataa    4020
tccatgaatg catttatatc ttaggaaaaa ttcttatcta tgtagtattt agaacatttt    4080
catgtgaggg gataaacaag gaagcacaga tgctttctga tagaaacttt ctctttaatt    4140
catctagaaa aaaaaaacct ctcaggaaaa tctctcttgc tctcctccca atgctctatt    4200
cagcatcttc tccctactta attctagatc ttttttctcta tgcctccttg ctgctgccct    4260
gctggctctg ctctatgcct ccccatgtca cttttctttg ctatctcacc gttaccttct    4320
ctgcctcact ctctgccttc ttctctgctt ctcacatggc caggctctgg acaattatag    4380
ttatatgtta cattctcata acacatgata tgtcacatag tttctctcag gctagggata    4440
```

```
tcacaatgac tggccaatga gcaagtggcc ttgcatgtag ctctaagttg gtgatggttc    4500
ccagacagta agtagccatt tggttgaaat ttgaggttgg gtagtacatg aagactgaat    4560
tttcttcaaa ctctggcctt gaaatagtaa acaacacct  atgaaaatga cgacctgtat    4620
ttgtctttag aggcaaccac atattgtctg cagggcctgc tttgaatttg ctctgaagtt    4680
agcttgtttg tgtaaaagga agaatcctat atcagcctga gaaatgtaaa atatcctagc    4740
atttcaagtc atcaaaatta tatggagagt ataaatcatc cttctgacta ttcatagtca    4800
tatttgtgtc caccaagtat aaaacacact accaaagggc tgtggaaaaa atcgccataa    4860
ctgttcttat tagggaggca tagcagtggt acctgaggaa gttacagcaa caaccagtca    4920
tccagtcaat aaccccatgg ctttgccact tggaggtacc caataatgtt tggctttgcc    4980
gagtaggact ccaacaaatt cagagggtca atttttaaat gctggttgtc actgctgaac    5040
agtcccattg ccctctgcat aattccacaa tggaaagctt tttacactga ttgccaatca    5100
ttaaacagcc tactcagcat aaacaggtat gatattattc tgcattttgt tacattacta    5160
gatgaattcc tatttcttcc tacaatagtg gaactgaaaa aagatacaca atcatactac    5220
ccctctacta atcttatgac ttatatcatt tcaattttca gaccataatg caaactattg    5280
accaaaacat gtgaagatga aaaatagaaa tgtagaataa tattacatat aaaaagaaaa    5340
ggcggactta ttttgtttta tttcttagca tgcatagcaa tacatgattt gaggtttata    5400
taataaaggg acaataaatc ttcaagaaac ttacccctac tgaattaaaa tattaaagaa    5460
ggtcacacat ttactcaaat atattagact actgggcaaa tagacatgaa agtagagtt     5520 aatattgagg taggccttct gtgaaatgtc taaggaaatt atgtttcata cagtgtgtaa    5580
ccaagtggga atcatatcag aaagcagtca aaagcttata ttacaagtaa cagatgcttg    5640
gttatatgac ctcccagagc ttgactgtct atacacaaaa agtggtgtta ataaaactgt    5700
aatttgggct atgttttttt aaatggcttc accaacatga aggaaggga  atgagcatgt    5760 catggatgct tagagattat gcttccagca agaagaattg agctttggct cttattacag    5820
aaacatgaca aggtgtgagt tttatttatt agaaattata taatatttta agctggggac    5880
taaaaatttt attgaaacaa acaggcaagg gataggcatg tactagaagc aaaaatagga    5940
tgtcaatgct gtaatgttat ttttggacc  aaaatagtat ttcctataga aatgacaatg    6000
atcttaggtt attattcttc ataaagatga caagttcaca agatatccta gttcattaaa    6060
atcgttttag tcatttaata gagtgctgtg atagattaca caaaggaaag cacttacgat    6120
gagaaataat gatatccaca attatttct  taattcttag aaacattcta ttgttatatc    6180
tcaatctcag aagccactta ttgctttatt attgaaacat atgaaattgt aagttatata    6240
ttgtctatgg tgacatttca aagaacatgt gacgtacagt gtagcacaga taagaaacat    6300
aactgcagct gaatcagtaa ctaaacttac atacattaaa tctgccatgt tggcaacagt    6360
gtgtgcacta ccaaaggatg tactaatgct cacgacactc ccctatgtca cccttttgttc   6420 atcattacat cataggtcta ttttgtttgc ttttgaaatc tagaccaagt cttttgtgtc    6480
tttccaagca cagagctcat taatttacct catagacttg ttaaacttct tctggttcat    6540
caattgaata gaaatactca ctactaatta tgtgagaccc tgccagtacc atagcacatg    6600
gataattttt acataaaaca tgcatacaag taagattatt cagactgaac atgaatttta    6660
gagaaatcag gaaggagtat atgggagtgg ttggagtgag actagagaaa tgtaattaaa    6720
ctataatctc aatacaaaga tctactaagc aaaaaacatg aaacattgtc attcaagtga    6780
aacatcagtc ttcaaattgg aaagatattt ttactaggaa aatgtctggt agatggttat    6840
```

```
tatctagaaa acacaaaaat tagaaaacgg taaactttaa taaaagaat aatacaatga    6900
gactacatga aaagttctta actaatgaaa caaatatctt gaaactttt tcttaaaagt     6960
ttaatatcaa taaccatcat ggaaattcaa attaaaacta tttacatatt acccctgaaa    7020
taataactaa tacccaataa aaataatata acaaaaaat ggcaatgcat gccatcatgg    7080
atttgggaga gagaatgttc attgcagttc tgaatggata ctggtgccac cacggtgaaa    7140
atctctgtat aggtccttcc aaaagctgaa aatagacata tcacaagacc tgccacacat    7200
ttttcaagca aatacccaaa ggactctacc tgactgcaga gacactttct cataaaatat    7260
tattgttgat ctattcataa tatctggaaa atagaaacag ccaagatgcc catcaactga    7320
ttaatagatg ataaaattat tgtacatttc agtgtaatat tattcagttt ttaagaaaaa    7380
tgaaattatg taataagcat gtaaatggat atatcttgaa acaaccattc cccattatat    7440
tacctaaaca ttgaaagtcc aaaatcatat gatctttta gtggatctac taatcttttg     7500
ctatatgtat tttattgaac tacccatgga tgtgagataa ttggtaacaa cagcacatgg    7560
gagagcatgg gatcattcaa ggaagattag agagaatgca tttttagga gataatggag     7620
gagcaataga aaggattaaa tgaggttact gatgaaagtg atggttagag aaggcaatat    7680
gaggagggat aactagcact tagggccttt tgaaaaagac atagagaaaa tactattgta    7740
gaaacttcct ataattggtg tatagttata tacaccaaag agctcagatg gagttacccct    7800
ataatggaaa tattaactac tttttatcac tgtgataaaa catcctgaac agagcaacat    7860
agattgggaa gcatttactt tggcttacag ttctaacggg ataaaaattc atgatgaaag    7920
aatgaatatg tcagcaaaca gcagtagcaa tggcctgaga agcaggtgag agctcacatc    7980
ttgaagtgta agaatgtagc agagagaaca aactgcaaat gaccagaaaa tgcttttgga    8040
tcagagccca tacccctctg actgacttct ccagaaattc tgaacaaata aaactcccca    8100
aacagagcca taactgaagg tccagtgtct gagactacta ggggtatttc ttattcaaac    8160
cactacaatg gggtgggggg agcaatcctc caagtaggca ctacacacag acaaataaaa    8220
actctagtaa ctggaatgga ttgacttatt tgaattactt gccagtggag ctacatagag    8280
cacaattatt gtatttaaat tacccttat gatcttacaa aacttgacag taagatcata    8340
ttgctaaaga aaccacatat ttgaatcagg gaacatggtg atatctagtt gttcttcaac    8400
tggaaacttc atgctttctg cccagcattc atgttgctgg aaagagcaat gtacactacc    8460
agtgtagaaa ttaaatcatc aatcttatca agatgtggat cctataagtt acaataaaaa    8520
ttagcctgat aagatatccc caccagaaga atattcacat aaatgctatg ggagcaacaa    8580
gctattttct aaattagctt taatcctatt ctacaagaga gaatccatat ctagaatagt    8640
tatagggatc aagaacccat ggcttgattg gtcataggcc caatgggaga tcctaatatt    8700
attgttctac aaaatgaaaa taactcctaa tgacttgttg ctgcagtaat aagttagtat    8760
gttgctcaac tctcacaaga gaagttttgt cttacaataa atggcaatta aagcagcccc    8820
acaagattta tatcataccg atctcctcat ggcctatgca tctagaagct aggaaacaaa    8880
gaggacccta agagagacat acatggtccc cctggagaag ggaaggggg caagacctcc    8940
aaagctaatt gggagcatgg gggagggag agggagttag aagaaagaga aggggataaa    9000
aggagggaga ggaggacaag agagagaagg aagatctagt caagagaaga tagaggagag    9060
caagaaaaga gataccatag tagagggagc cttgtatgtt taaatagaaa actggcacta    9120
gggaattgtc caaagatcca caaggtccaa ctaataatct aagcaatagt cgagaggcta    9180
```

```
ccttaaaagc ctttctctga taatgagatt gatgactacc ttatatacca tcctagagcc   9240
ttcatccagt agctgatgga agcagaagca gacatctaca gctaaacact gagctagttg   9300
cagacaggga ggagtgatga gcaaagtcaa gaccaggctg gagaaacaca cagaaacagc   9360
agacctgaaa aaaatgttgc acatggaccc cagactgata gctgggagtc cagcatagga   9420
cttttctaga aaccctgaat gaggatatca gtttggaggt ctggttaatc tatggggaca   9480
ctggtagtgg atcaatattt atccctagtt catgactgga atttgggtac ccattccaca   9540
tggaggaatt ctctgtcagc ctagacacat gggggaggtt ctaggtcctg ctccaaataa   9600
tgtgttagac tttgaagaac tcccttgaga agactcaccc tccctgggga gcagaaaggg   9660
gatgggatga gggttggtga gggacaggag aggagggag ggtgagggaa ctgggattga    9720
caagtaaatg atgcttgttt ctaatttaaa tgaataaagg aaagtaaaa gaagaaaaga    9780
aaacaggcca aagattata aagacagag gtggtgggtg actataaaga aacactatta     9840
tctaaataaa aatatgtcag aagcacacat gaacttatag tgtttatgaa agtatgtata   9900
ataactacat aatctcaagc caagaaaaaa atatcatctt tcagtgatga aggtgatttt   9960
atttctccca gaattaaagc caaagaccta atgaaagtaa ttatcttcaa aaggttgaaa  10020
atacatactt tgcaatacac agatctgcct agaaatctca tgttcacaat acacatgatg  10080
ctcaattgaa ttccattcaa tgttacagtt tagataaaca gtttgtagat aaactcacaa  10140
tgtatcattt cttttattt tttgaccaaa cagcttctca tctgttattc agaataattc    10200
ctcgatggca ggatatccat cccaattggg ggaaggggag aatttgaaga aaacctagac  10260
cacatacata tttgccattg ggaaacaaag tctaaaatga tgttgttcac atcttctcta  10320
ctagtcctct ccccgtccca aagaaccttg gtatatgtgc ctcatttac agagagagga    10380
aagcaggaac tgagcatccc ttacttgcca tcctcaaccc aaaatttgca tcattgctca  10440
gctctgccct tctcatatga cagttacaag tcaaggcttc caaagtccct ctgtcatgtt  10500
tggtgtcaat agtttataca gatgacttca tgtcttcata tctaatgtct tatatagatt  10560
aatattaaac aatgttattt ctctaaccac attttaaatt aatttaaaaa tccattaatt  10620
gtgtctataa aatgcagaca gagtgctgag acacaatata agcctgatga tctgaatttg  10680
aaactcacac ccaccacatg gagaatcaac ttccaaaaat tttcctatta cttccacact  10740
tacaccattg tacaaacaca ataataatga acaaaatgaa atgaaataaa aaattaagtc  10800
tctgtaggta atgctactgt gcagcaaaag taaaaatggc agcttaagct tgctttatgg  10860
ttacacttta ccatcttcca ttaattataa ggacttcaat catggcagaa ctatgctgtt  10920
attgtctcag tgtaacctaa ccaggtgttc cagatgttct taatgtggac acctaaacta  10980
tttgatattt gggttaagat cttccctct ttcagaagaa acctcaggac agagggaatc   11040
ttgtctttta atttgagtc tgtagacttt ttccatttca aatatacatg aaacaagtga    11100
tgaagaaaat taatcaaaag gtgggaattg caatgatatt aggttcaata ttaagcttca  11160
atattatcat ggaatcgcct gttatacact gagtgtttgg caataaggga tttttagaag  11220
aaggagtttt tattctcaac aggttcctta agtttagctc aaataaatct aagcaatcca  11280
ctctagaatt aaatagtttc ctaagggcac agctatgaat agagctcaat ttacatataa  11340
aattttgttc accatttatg tcattccagt tttcattagt acaaggaaaa tacaaaatat  11400
ttagatgtca atatcaagtg aatagttcat ctccttttt aatatatatc acctaaatca   11460
ccattttctc agaaaaatct ggcctgaagt tctgtctgga acttcaacat gaaaaatatg  11520
cacagcttgc tattataaat cctagttgat ttttaagatt catgtctggt gtctgactca  11580
```

```
gaggggccag aggctagaca aatattttt  gaatcttcat tgtgaagatt tttaatgatt  11640
attttaatat aaataacaaa gatgatggat aatgtaactt tgtacagttc atagacgctg  11700
aactactttg tgcttaaaat gttagttccc tatcataaat gataggtgat aagtgtatgt  11760
ttaatacttt ccctctgagc tatattcatg tactagagaa ttattttaaa catgaaagaa  11820
ctgtgtttat agtctcagct cctgagaact ggtccaacct taggcaggtg aatgccagga  11880
gcaacgtttt tcttctacag aggatgcttt gctgccaagc aacctggttg tgtggaaatg  11940 ttccttttt  aatcaagttt aaagggtctt catcatgctg ttgctccaca tattttcagg  12000
ttagagcttg gtccttggag tattatcttt taccagaaaa ttcatagtat tctttcaata  12060
actaacaact aaacttttcg ataaaaaaga attggaattt caattttaaa gcctgagtaa  12120
aattcttgtg aatcaggata ttttatttta agtcttatct tttaaaaagt tattttattt  12180
tttaaaaaat tataatatac tttcataatt tccctccttc acttttcttt acaaacactt  12240
ctatagatca ccatgtgttt ttttttttac atttatggcc tctttctgtt cattgttatt  12300
acatacaaat agtcttgcct atagaagaac accacaattt gttacctgat aacaaattat  12360
caacccttaa aacctacaaa ctattgatat tactgaaaag actatactta tagatgtaaa  12420
gatatatgtg tgtgcacata tatagataca catatatgta ggattttaa  ttttagattt  12480 tagacatcaa aattatttat atgactgaga aactagacac tataaatgag cattcagtat  12540
tcaacaccgt gattttagat attgtcacaa tgacagaaaa ttttcttata gaaaattta   12600 agttttgtga ttgctctgtg cacttagtga agtctcacag aaaaagaatc atagtatttt  12660
tagtttataa taaaaagtac atataattaa aatggttggc acaaacaac  atttgagcat  12720 ttttcctatt tactatcaag tagtatcatt ttgaaataat aatttgacta gtttcaaaaa  12780
tgaaaacaaa atttaaacta aatgcctaat ctagcctgat aacattttta tgaatgaaat  12840
tattcaatag tgttatcaat taggggccca aaacttttcc taaaataaaa ctttaatt   12900 ttttccattt ttatttaaat tagaaacaaa attgttttac atgtaaatca gagtttcctc  12960
accctcccct tctccctgtc cctcactaac accctacttg tcccatacca tttctgctcc  13020
ccagggaggg tgaggccttc catggggaaa cttcagagtc tgtctatcct ttcggatagg  13080
gcctaggccc tcacccattt gtctaggcta aggctcacaa agtttactcc tatgctagtg  13140
ataagtactg atctactaca agagacacca tagatttcct aggcttcctc actgacaccc  13200
atgttcatgg ggtctggaac aatcatatgc tagtttccta ggtatcagtc tggggaccat  13260
gagctccccc ttgttcaggt caactgtttc tgtgggtttc accaccctgg tcttgactgc  13320
tttgctcatc actcctccct ttctgtaact gggttccagt acaattccgt gtttagctgt  13380
gggtgtctac ttctactttc atcagcttct gggatggagc ctctaggata gcatacaatt  13440
agtcatcatc tcattatcag ggaagggcat ttaaagtagc ctctccattg ttgcttggat  13500
tgttagttgg tgtcatcttt gtagatctct ggacatttcc ctagtgccag atatctcttt  13560
aaacctacaa gactacctct attatggtat ctcttttctt gctctcgtct attcttccag  13620
acaaaatctt cctgctccct tatattttcc tctcccctcc tcttctcccc ttctcattct  13680
cctagatcca tcttcccttc ccccatgctc ccaagagaga tgttgctcag gagatcttgt  13740
tccttaaccc ttttcttggg gatctgtctc tcttagggtt gtccttgttt cctagcttct  13800
ctggaagtgt ggattgtaag ctggtaatca tttgctccat gtctaaaatc catatatgag  13860
tgatgtttgt cttttttgtga ctgggttacc tcactcaaaa tggtttcttc catatgtctg  13920
```

```
tggatttcaa tagcacaaac aacatacagt atcttggggc aacactaacc aaacaagtga    13980
aagaccagta tagcaagaac tttgagttta agaaagaaa ttaaagaaga taccagaaaa     14040
tggaaagatc tcccatgctc tttgataggc agaatcaaca tagtaaaaat ggcaatcttg    14100
ccaaaatcca tctacagact caatgcaatc cccattaaat accagcacac ttcttcacag    14160
acctgaaaga ataatactta actttatatg gagaaacaaa agacccagga taggccaaac    14220
aaccctgtac aatgaaggca cttccagagg catccccatc cctgacttca agctctatta    14280
tagagtaata atcctgaaaa cagcttggta atggcacaaa aatagacagg tagaccaatg    14340
gaattgagtt gaaaaccctg atattaaccc acatatctat gaacacctga ctttgacaaa    14400
gaagctaagg ttatacaatg taagaaagaa agcatcttca acaaatcgtg ctggcataac    14460
tggatgctgg catgtagaag actgcagata gatccatgtc taatgccatg cacaaaactt    14520
aagtccaaat ggatcaaaaa cctcaacata atccagcca cactgaacct catagaagag      14580
aaagtgggaa gtatccttga ataaattggt acaggagacc acatcttgaa cttaacacca    14640
gtagcacaga caatcagatc aataatcaat aaatgggacc tcctgaaact gagaagcttc    14700
tgtaaggcaa tggataagtc aacaggacaa atggcagcc cacggaatgg gaaaagatat      14760
tcaccaatcc tatatctgac agagggctgc tctctatttg caaagaacac aataagctag    14820
tttttaaaac accaattaat ccgattataa agttgggtag agaactaaat aaagaattgt    14880
taacagagca atctaacttg gcagaaagac acataagaaa gtgctcacca t              14931

<210> SEQ ID NO 3
<211> LENGTH: 4001
<212> TYPE: DNA
<213> ORGANISM: Cricetulus griseus

<400> SEQUENCE: 3
ccaagatgcc catcaactga ttaatagatg ataaaattat tgtacatttc agtgtaatat        60
tattcagttt ttaagaaaaa tgaaattatg taataagcat gtaaatggat atatcttgaa       120
acaaccattc cccattatat tacctaaaca ttgaaagtcc aaaatcatat gatctttta         180 gtggatctac taatcttttg ctatatgtat tttattgaac tacccatgga tgtgagataa       240
ttggtaacaa cagcacatgg gagagcatgg gatcattcaa ggaagattag agagaatgca      300
ttttttagga gataatggag gagcaataga aaggattaaa tgaggttact gatgaaagtg      360
atggttagag aaggcaatat gaggagggat aactagcact tagggccttt tgaaaaagac     420
atagagaaaa tactattgta gaaacttcct ataattggtg tatagttata tacaccaaag      480
agctcagatg gagttaccct ataatggaaa tattaactac tttttatcac tgtgataaaa     540
catcctgaac agagcaacat agattgggaa gcatttactt tggcttacag ttctaacggg    600
ataaaaattc atgatgaaag aatgaatatg tcagcaaaca gcagtagcaa tggcctgaga    660
agcaggtgag agctcacatc ttgaagtgta agaatgtagc agagagaaca aactgcaaat    720
gaccagaaaa tgctttttgga tcagagccca tacccctctg actgacttct ccagaaattc    780
tgaacaaata aaactcccca acagagccaa taactgaagg tccagtgtct gagactacta    840
ggggtatttc ttattcaaac cactacaatg gggtgggggg agcaatcctc caagtaggca    900
ctacacacag acaaataaaa actctagtaa ctggaatgga ttgacttatt tgaattactt      960
gccagtggag ctacatagag cacaattatt gtatttaaat tacccttat gatcttacaa       1020 aacttgacag taagatcata ttgctaaaga accacatat ttgaatcagg gaacatggtg       1080
atatctagtt gttcttcaac tggaaacttc atgctttctg cccagcattc atgttgctgg       1140
```

```
aaagagcaat gtacactacc agtgtagaaa ttaaatcatc aatcttatca agatgtggat    1200
cctataagtt acaataaaaa ttagcctgat aagtatccc caccagaaga atattcacat     1260
aaatgctatg ggagcaacaa gctattttct aaattagctt taatcctatt ctacaagaga    1320
gaatccatat ctagaatagt tatagggatc aagaacccat ggcttgattg gtcataggcc    1380
caatgggaga tcctaatatt attgttctac aaaatgaaaa taactcctaa tgacttgttg    1440
ctgcagtaat aagttagtat gttgctcaac tctcacaaga gaagttttgt cttacaataa    1500
atggcaatta aagcagcccc acaagattta tatcataccg atctcctcat ggcctatgca    1560
tctagaagct aggaaacaaa gaggaccta agagagacat acatggtccc cctggagaag     1620 ggaaggggg caagacctcc aaagctaatt gggagcatgg gggagggag agggagttag      1680 aagaaagaga aggggataaa aggagggaga ggaggacaag agagagaagg aagatctagt    1740
caagagaaga tagaggagag caagaaaaga gataccatag tagagggagc cttgtatgtt    1800
taaatagaaa actggcacta gggaattgtc caaagatcca caaggtccaa ctaataatct    1860
aagcaatagt cgagaggcta ccttaaaagc cttctctga taatgagatt gatgactacc     1920
ttatatacca tcctagagcc ttcatccagt agctgatgga agcagaagca gacatctaca    1980
gctaaacact gagctagttg cagacaggga ggagtgatga gcaaagtcaa gaccaggctg    2040
gagaaacaca cagaaacagc agacctgaaa aaaatgttgc acatggaccc cagactgata   2100
gctgggagtc cagcatagga cttttctaga aaccctgaat gaggatatca gtttggaggt    2160
ctggttaatc tatggggaca ctggtagtgg atcaatattt atccctagtt catgactgga    2220
atttgggtac ccattccaca tggaggaatt ctctgtcagc ctagacacat ggggagggtt    2280
ctaggtcctg ctccaaataa tgtgttagac tttgaagaac tcccttgaga agactcaccc    2340
tccctgggga gcagaaaggg gatgggatga gggttggtga gggacaggag aggagggag    2400 ggtgagggaa ctgggattga caagtaaatg atgcttgttt ctaatttaaa tgaataaagg    2460
aaaagtaaaa gaagaaaaga aaacaggcca aaagattata aaagacagag gtggtgggtg    2520
actataaaga aacactatta tctaaataaa aacatgtcag aagcacacat gaacttatag    2580
tgtttatgaa agtatgtata ataactacat aatctcaagc caagaaaaaa atatcatctt    2640
tcagtgatga aggtgatttt atttctccca gaattaaagc caaagaccta atgaaagtaa    2700
ttatcttcaa aaggttgaaa atacatactt tgcaatacac agatctgcct agaaatctca    2760
tgttcacaat acacatgatg ctcaattgaa ttccattcaa tgttacagtt tagataaaca    2820
gtttgtagat aaactcacaa tgtatcattt ctttttattt tttgaccaaa cagcttctca    2880
tctgttattc agaataattc ctcgatggca ggatatccat cccaattggg ggaaggggag    2940
aatttgaaga aaacctagac cacatacata tttgccattg ggaaacaaag tctaaaatga    3000
tgttgttcac atcttctcta ctagtcctct ccccgtccca aagaaccttg gtatatgtgc    3060
ctcattttac agagagagga aagcaggaac tgagcatccc ttacttgcca tcctcaaccc    3120
aaaatttgca tcattgctca gctctgccct tctcatatga cagttacaag tcaaggcttc    3180
caaagtccct ctgtcatgtt tggtgtcaat agtttataca gatgacttca tgtcttcata    3240
tctaatgtct tatatagatt aatattaaac aatgttattt ctctaaccac attttaaatt    3300
aatttaaaaa tccattaatt gtgtctataa aatgcagaca gagtgctgag acacaatata    3360
agcctgatga tctgaatttg aaactcacac ccaccacatg gagaatcaac ttccaaaaat    3420
tttcctatta cttccacact tacaccattg tacaaacaca ataataatga acaaaatgaa    3480
```

-continued

```
atgaaataaa aaattaagtc tctgtaggta atgctactgt gcagcaaaag taaaaatggc    3540
agcttaagct tgctttatgg ttacacttta ccatcttcca ttaattataa ggacttcaat    3600
catggcagaa ctatgctgtt attgtctcag tgtaacctaa ccaggtgttc cagatgttct    3660
taatgtggac acctaaacta tttgatattt gggttaagat cttccctct ttcagaagaa     3720 acctcaggac agagggaatc ttgtctttta attttgagtc tgtagacttt ttccatttca    3780
aatatacatg aaacaagtga tgaagaaaat taatcaaaag gtgggaattg caatgatatt    3840
aggttcaata ttaagcttca atattatcat ggaatcgcct gttatacact gagtgtttgg    3900
caataaggga tttttagaag aaggagtttt tattctcaac aggttcctta agtttagctc    3960
aaataaatct aagcaatcca ctctagaatt aaatagtttc c                        4001
```

COMPOSITIONS AND METHODS FOR MAKING ANTIBODIES BASED ON USE OF AN EXPRESSION-ENHANCING LOCUS

CROSS REFERENCE TO RELATED APPLICATION

This application claims the benefit of priority from U.S. Provisional Application No. 62/325,385, filed Apr. 20, 2016, the entire contents of which are incorporated herein by reference.

FIELD OF THE DISCLOSURE

This disclosure relates to site-specific integration and expression of recombinant proteins in eukaryotic cells. In particular, the disclosure relates to compositions and methods for improved expression of antigen-binding proteins such as bispecifc antibodies in eukaryotic cells, particularly Chinese hamster (*Cricetulus griseus*) cell lines, by employing an expression-enhancing locus.

BACKGROUND ART

Cellular expression systems aim to provide a reliable and efficient source for the manufacture of a given protein, whether for research or therapeutic use. Recombinant protein expression in mammalian cells is a preferred method for manufacturing therapeutic proteins due to, for example, the ability of mammalian expression systems to appropriately post-translationally modify recombinant proteins.

Despite the availability of various expression systems, the challenge of efficient gene transfer and stability of the integrated gene for expression of a recombinant protein still exists. For long-term expression of a target transgene, one consideration is minimal disruption of cellular genes to avoid changes in the phenotype of the cell line.

Engineering stable cell lines to accommodate multiple genes for expression, such as multiple antibody chains as in multispecific antibodies, is particularly challenging. Wide variations in expression levels of integrated genes may occur. Integrating additional genes may lead to greater variation in expression and instability due to the local genetic environment (i.e., position effects). Expression systems for the production of multispecific antigen-binding proteins often requires the expression of two or more different immunoglobulin chains intended to pair as a specific multimeric format, and can often weigh in favor of homodimer production, rather than the desired heterodimer or multimer combination. Accordingly, there is a need in the art for improved mammalian expression systems.

SUMMARY OF THE DISCLOSURE

In one aspect, a cell is provided that contains an exogenous nucleic acid sequence integrated at a specific site within an enhanced expression locus, wherein the exogenous nucleic acid sequence encodes a bispecific antigen-binding protein.

In some embodiments, the exogenous nucleic acid sequence includes a first exogenous nucleic acid containing a nucleotide sequence encoding a first light chain fragment (LCF), a second exogenous nucleic acid containing a nucleotide sequence encoding a first heavy chain fragment (HCF), and a third exogenous nucleic acid containing a nucleotide sequence encoding a second HCF (or denoted as HCF* where the second HCF is different from the first HCF), wherein the first and second HCFs and the first LCF form a bispecific antigen-binding protein. In certain embodiment, the first and second HCFs and the first LCF contain at least two variable regions and two CH3 constant domains of a bispecific antigen-binding protein. In some embodiments, the two variable regions are different. In some embodiments, the two CH3 regions are different. In some embodiments, each exogenous nucleic acid sequence is integrated simultaneously at a specific site within the enhanced expression locus.

In some embodiments, the nucleotide sequence encoding the first HCF encodes amino acids from a first constant region (e.g., encodes one or more of CH1, CH2, hinge or CH3 domain), and the nucleotide sequence encoding the second HCF encodes amino acids from a second constant region. The amino acids from a first constant region can be the same or different from the amino acids from a second constant region. In specific embodiments, the nucleotide sequence encoding the first HCF encodes a first CH3 domain, and the nucleotide sequence encoding the second HCF encodes a second CH3 domain, wherein the first and second CH3 domains can be the same or different. In some embodiments, the first and second CH3 domains differ in at least one amino acid position; e.g., one of the two CH3 domains is a human IgG CH3 domain, and the other one is a modified human IgG CH3 domain, and the two CH3 domains have different Protein A binding characteristic. In other embodiments, the nucleotide sequences encoding the first and second CH3 domains differ from each other in that one of the nucleotide sequences has been codon modified.

In other specific embodiments, the nucleotide sequence encoding the first HCF encodes a first heavy chain variable (VH) region, and the nucleotide sequence encoding the second HCF encodes a second VH region, wherein the first and second heavy chains can have the same or different VH regions. In another embodiment, the first and second VHs can be linked to the same or different constant regions.

In some embodiments, the nucleotide sequence encoding the first LCF encodes a first light chain variable (VL) region.

In some embodiments, the exogenous nucleic acid sequence contains an additional exogenous nucleic acid that includes a nucleotide sequence encoding a second LCF, such as a second light chain variable (VL) region. In some embodiments, the nucleotide sequence encoding the second VL region also encodes a second light chain constant region.

The relative positions of the multiple exogenous nucleic acids at the locus can vary. In some embodiments, the LCF encoding nucleic acid is located upstream or downstream relative to both HCF-encoding nucleic acids.

In some embodiments, each of the HCF or LCF-encoding sequence is independently linked to a transcriptional regulatory sequence. In specific embodiments, the first exogenous nucleic acid further includes a first promoter operably linked to the nucleotide sequence encoding a first LCF, the second exogenous nucleic acid further comprises a second promoter operably linked to the nucleotide sequence encoding a first HCF, and a third exogenous nucleic acid comprising a third promoter operably linked to the nucleotide sequence encoding a second HCF, wherein the first, second and third promoters are the same or different, and/or said promoters are the same or different from the fourth promoter to which the fourth exogenous nucleic acid is operably linked. In some embodiments, the first, second and third promoters are the same.

In some embodiments, the exogenous nucleic acid sequence at the integration site further includes recombinase recognition sites, for example, a first recombinase recognition site (RRS) located 5' relative to the first exogenous nucleic acid, and a second recombinase recognition site (RRS) located 3' relative to both the second and third exogenous nucleic acids, wherein the first and second RRSs are different. In some embodiments, a third RRS is also included and located 3' relative to the first exogenous nucleic acid, and 5' relative to one or both the second and third exogenous nucleic acids, wherein the third RRS is different from the first and second RRSs.

In some embodiments, the exogenous nucleic acid sequence can include a fourth exogenous nucleic acid containing a selectable marker gene. In specific embodiments, the fourth exogenous nucleic is located 3' relative to the first exogenous nucleic acid. In certain embodiments, the fourth exogenous nucleic acid is integrated as a split gene. In other embodiments, the fourth exogenous nucleic acid, or selectable marker, is located 3' of the third RRS, which is 3' of a fourth promoter which is operably linked to the fourth exogenous nucleic acid. In some embodiments, the selectable marker gene comprises the third RRS which has been inserted, optionally inserted within an intron of the selectable marker gene, wherein the third RRS is different from the first and second RRS.

In certain embodiments, the order of the exogenous nucleic acids at a locus can be: from 5' to 3', the first exogenous nucleic acid (encoding LCF), the fourth exogenous nucleic acid (encoding selectable marker), the second exogenous nucleic acid (encoding first HCF), and the third exogenous nucleic acid (encoding second HCF); and in some particular embodiments, the second exogenous nucleic acid contains a nucleotide sequence encoding a modified CH3 domain of a human IgG, and the third exogenous nucleic acid comprises a nucleotide sequence encoding the native CH3 domain of the human IgG.

In certain embodiments, the order of the exogenous nucleic acids at a locus is: from 5' to 3', the first exogenous nucleic acid (encoding LCF), the second exogenous nucleic acid (encoding first HCF), the fourth exogenous nucleic acid (encoding selectable marker), and the third exogenous nucleic acid (encoding second HCF), wherein the second exogenous nucleic acid comprises a nucleotide sequence encoding the native CH3 domain of a human IgG, and the third exogenous nucleic acid comprises a nucleotide sequence encoding a modified CH3 domain of the human IgG.

In some embodiments, the promoters linked to the HCF or LCF-coding sequences are the same, and are different from the promoter to which the selectable marker gene is operably linked.

In some embodiments, the bispecific antigen-binding protein specifically binds to a T-cell antigen and to a tumor cell antigen. Other suitable dual antigen specificities are also provided.

In some embodiments, the enhanced expression locus is selected from a locus comprising a nucleotide sequence at least 90% identical to SEQ ID NO: 1, or a locus comprising a nucleotide sequence at least 90% identical to SEQ ID NO: 2.

In various embodiments, the cell is a CHO cell.

In another aspect, vectors are provided that are designed for site-specific integration of multiple exogenous nucleic acids.

In some embodiments, this disclosure provides a set of vectors which set includes a first vector containing from 5' to 3': a first RRS, a first nucleic acid containing a nucleotide sequence encoding a first LCF, and a third RRS; and a second vector containing from 5' to 3', the third RRS, a second nucleic acid containing a nucleotide sequence encoding a first VH region, a second RRS; wherein either the first or the second nucleic acid further comprises a nucleotide sequence encoding a second HCF; and wherein the first and second HCF, and the first LCF, form a bispecific antigen binding protein.

In some embodiments, the nucleotide sequence encoding the second HCF is included in the first nucleic acid, optionally located downstream of the nucleotide sequence encoding the first LCF. In other embodiments, the nucleotide sequence encoding the second HCF is included in the second nucleic acid.

In some embodiments, the nucleotide sequence encoding the first HCF encodes a first chimeric constant region (e.g., encodes one or more of CH1, hinge CH2, or CH3 domain, or fragments thereof, from any isotype), and the nucleotide sequence encoding the second HCF encodes a second chimeric constant region. Examples of a chimeric constant region is described in PCT International Publication No. WO 2014/121087 A1, published on Aug. 7, 2014, incorporated herein by reference. The amino acids from a first constant region can be the same or different from the second chimeric constant region. In specific embodiments, the nucleotide sequence encoding the first HCF encodes a first CH3 domain, and the nucleotide sequence encoding the second HCF encodes a second CH3 domain, wherein the first and second CH3 domains can be the same or different. In some embodiments, the first and second CH3 domains differ in at least one amino acid position; e.g., one of the two CH3 domains is a human IgG CH3 domain, and the other one is a modified human IgG CH3 domain, and the two CH3 domains have different Protein A binding characteristic. In other embodiments, the nucleotide sequences encoding the first and second CH3 domains differ from each other in that one of the nucleotide sequences has been codon modified.

In other specific embodiments, the nucleotide sequence encoding the first VH region encodes a first heavy chain, and the nucleotide sequence encoding the second VH region encodes a second heavy chain, wherein the first and second heavy chains can have the same or different constant regions.

In some embodiments, the nucleotide sequence encoding the first LCF encodes a first light chain variable region (VL).

In some embodiments, each of the LCF- or HCF-encoding sequences is independently linked to a transcriptional regulatory sequence, such as a promoter. In specific embodiments, the promoter linked to a first HCF-coding sequence and the promoter linked to a second HCF-coding sequence are the same. In specific embodiments, the promoters linked to LCF(s) and HCF(s) are all the same.

In some embodiments, the first nucleic acid in the first vector further contains a 5' portion of a selectable marker gene, located at 5' to the third RRS in the first vector; and the second nucleic acid further contains the remaining 3' portion of the selectable marker gene, located 3' to the third RRS in the second vector—that is, the selectable marker gene is split into the two vectors. In other embodiments, selectable marker and the promoter to which it is operably linked are split between the two vectors, in other words the promoter and selectable marker gene are located on different vectors. In certain embodiments, the promoter operably linked to the marker gene is located in the first vector 5' to a third RRS, and the marker gene is located 3' of the third RRS in the second vector, and is 5' of a second promoter operably linked to a second nucleic acid and a third promoter operably linked to third nucleic acid. In some embodiments, the third RRS in the first vector is present within a 5' portion of an intron of the selectable marker gene; and the third RRS in the second vector is present within a 3' portion of an intron of the selectable marker gene.

In specific embodiments, the first vector includes, from 5' to 3', the first RRS, the first nucleic acid, and the third RRS; and the second vector includes, from 5' to 3', the third RRS, the second nucleic acid wherein the second nucleic acid contains the nucleotide sequence encoding a first HCF and the nucleotide sequence encoding a second HCF, and a second RRS. In other specific embodiments, the first vector includes from 5' to 3', the first RRS, the first nucleic acid wherein the first nucleic acid comprises the nucleotide sequence encoding a first HCF and the nucleotide sequence encoding a second HCF region, and the third RRS; and the second vector includes 5' to 3', the third RRS, the second nucleic acid wherein the second nucleic acid comprises a nucleotide sequence encoding a first HCF region, and a second RRS. In any of these specific embodiments, the first nucleic acid can further include a 5' portion of a selectable marker gene, located at 5' to the third RRS in the first vector, and the second nucleic acid further comprises the remaining 3' portion of the selectable marker gene, located 3' to the third RRS in the second vector; and wherein optionally the third RRS in the first vector is present within a 5' portion of an intron of the selectable marker gene, and the third RRS in the second vector is present within a 3' portion of an intron of the selectable marker gene.

In some embodiments, the vector set can include an additional vector or vectors; for example, a vector containing one or more RRSs and a nucleotide sequence encoding a second LCF, or a vector encoding one or more recombinases that recognize the RRSs.

In other embodiments, this disclosure provides a vector designed to achieve site-specific integration of multiple exogenous nucleic acids via homologous recombination based on homology arms. In some embodiments, the vector contains an exogenous nucleic acid sequence that encodes a bispecific antigen-binding protein, flanked by a 5' homology arm and a 3' homology arm for integration into an expression enhancing locus of a cell.

In a further aspect, this disclosure provides a system that includes a combination of a cell and one or more vectors, and that can be utilized to make cells having integrated within an expression enhancing locus exogenous nucleic acids that together encode a bispecific antigen binding protein.

In certain embodiments, a system is provided that includes a cell and a set of vectors, wherein the cell contains, integrated within an enhanced expression locus of its genome a set of RRSs that are different from one another and spaced between one or more exogenous nucleic acids, such as selection markers, for recombinant exchange with genes of interest in a set of vectors; and wherein the RRSs in the set of vectors comprise the same arrangement as the RRSs in the cell.

In some embodiments, a system is provided that includes a cell and a set of vectors, wherein the cell contains, integrated within an enhanced expression locus of its genome from 5' to 3': a first RRS, a first exogenous nucleic acid, a second RRS, a second exogenous nucleic acid, and a third RRS, wherein the three RRSs are different from one another, wherein the set of vectors includes a first vector containing from 5' to 3', the first RRS, a first nucleic acid containing a nucleotide sequence encoding a first immunoglobulin chain or fragment thereof, and the second RRS; a second vector containing the second RRS, a second nucleic acid containing a nucleotide sequence encoding a second immunoglobulin chain or fragment thereof, and the third RRS; and wherein either the first nucleic acid or the second nucleic acid further includes a nucleotide sequence encoding a third immunoglobulin chain or fragment thereof. Upon introduction of the vectors into the cell, the first and second nucleic acids in the vectors integrate into the enhanced expression locus through recombination mediated by the first, second and third RRSs.

In some embodiments, the first exogenous nucleic acid in the cell contains a first selectable marker gene, and the second exogenous nucleic acid in the cell contains a second selectable marker gene, wherein the first and second selectable marker genes are different. The selectable markers exchange with the integrated exogenous nucleic acids in the cell.

In some embodiments, the first vector includes from 5' to 3', the first RRS, the first nucleic acid containing the nucleotide sequence encoding the first LCF, and the third RRS; and the second vector containing 5' to 3', the third RRS, the second nucleic acid, wherein the second nucleic acid containing both the nucleotide sequence encoding the first HCF and the nucleotide sequence encoding the second HC, and the second RRS. In other embodiments, the first vector contains from 5' to 3', the first RRS, the first nucleic acid containing the nucleotide sequence encoding the first LCF and the nucleotide sequence encoding the second HCF, and the third RRS; and the second vector contains 5' to 3', the third RRS, the second nucleic acid containing the nucleotide sequence encoding the first HCF, and the second RRS.

In some embodiments, the first vector includes from 5' to 3', the first RRS, the first nucleic acid containing the nucleotide sequence encoding the first HCF, and the third RRS; and the second vector containing 5' to 3', the third RRS, the second nucleic acid, wherein the second nucleic acid containing both the nucleotide sequence encoding the first LCF and the nucleotide sequence encoding the second HCF, and the second RRS. In other embodiments, the first vector contains from 5' to 3', the first RRS, the first nucleic acid containing the nucleotide sequence encoding the first HCF and the nucleotide sequence encoding the second HCF, and the third RRS; and the second vector contains 5' to 3', the third RRS, the second nucleic acid containing the nucleotide sequence encoding the first LCF, and the second RRS. In any of these embodiments, the first nucleic acid in the first vector can further include a promoter located at 5' to the third RRS, and the second nucleic acid in the second vector further includes the selectable marker gene to which the promoter will be operably linked, located 3' to the third RRS. In other embodiments, the first nucleic acid in the first vector can further include a 5' portion of a selectable marker gene, located at 5' to the third RRS, and the second nucleic acid in the second vector further includes the remaining 3' portion of the selectable marker gene, located 3' to the third RRS; wherein optionally the third RRS in the first vector is present within a 5' portion of an intron of the selectable marker gene; and the third RRS in the second vector is present within a 3' portion of an intron of the selectable marker gene.

In some embodiments, the nucleotide sequence encoding the LCF is operably linked to a first promoter, the nucleotide sequence encoding the first HCF is operably linked to a second promoter, and the nucleotide sequence encoding the second HCF is operably linked to a third promoter, wherein the first, second, and third promoters are the same, and are different from the promoter to which a selectable marker gene, if present in one of the vectors, is operably linked.

In some embodiments, the nucleotide sequence encoding the first HCF encodes a first CH3 domain, and the nucleotide sequence encoding the second HCF encodes a second CH3 domain, wherein the first and second CH3 domains can be the same or different. In some embodiments, one of the two CH3 domains is the native CH3 domain of a human IgG, and the other CH3 domain is a modified CH3 domain of the human IgG. In specific embodiments, the nucleotide sequence encoding the modified CH3 domain is in the first vector (i.e., the vector encoding the first LCF), optionally downstream of the nucleotide sequence encoding the first LCF. In other specific embodiments, the nucleotide sequence encoding the modified CH3 domain is in the second vector and is upstream of the nucleotide sequence encoding the unmodified CH3 domain.

In another aspect, this disclosure provides methods for making a bispecific antigen-binding protein.

In some embodiments, the method includes providing a system described herein that contains a cell having RRSs and a set of vectors containing multiple exogenous nucleic acids that together encode a bispecific antigen-binding protein and RRS matching the RRSs in the cell; introducing the vectors into the cell by transfection; selecting a transfected cell where the exogenous nucleic acids in the vectors have integrated into an enhanced expression locus of the cell through recombination mediated by the RRSs; expressing the polypeptides encoded by the nucleic acids in the transformed cell; and obtaining the bispecific antigen-binding protein from the transfected cell.

In some embodiments, the method can include a cell containing an exogenous nucleic acid sequence that encodes a bispecific-antigen binding protein integrated within an expression enhancing locus, expressing the bispecific antigen-binding protein from the exogenous nucleic acid sequence; and obtaining the bispecific antigen-binding protein from the cell.

DETAILED DESCRIPTION

Definitions

Figure 1:
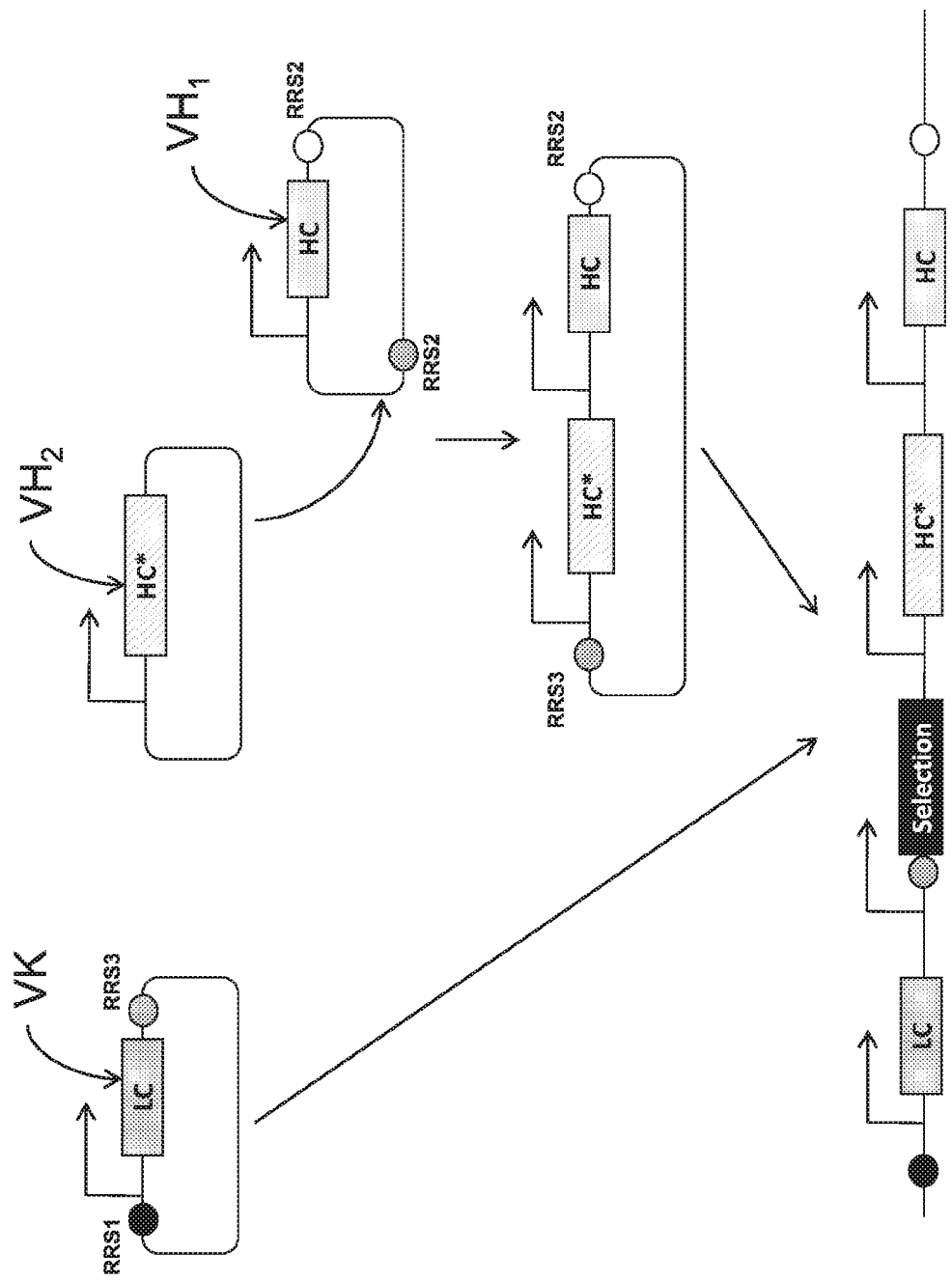
FIG. 1. An exemplary bispecific cloning strategy for integration within an expression enhancing locus. A light chain ("LC") vector, e.g. a common light chain, and a dual heavy chain ("HC") vector (with "*" indicating that the two HCs are different, e.g. HC* contains a modification in the CH3 domain and/or is codon-modified) are made by cloning variable regions of antibody of interest into appropriate vectors. The 3' RRS site of the LC vector and the 5' RRS site of the dual HC vector are the same and included in a split intron of a hygromycin resistance gene, engineered to combine and excise the intron to allow expression of the protein encoded by the hygromycin resistance gene for efficient selection of recombinants. The arrows represent promoters.
Figure 2:
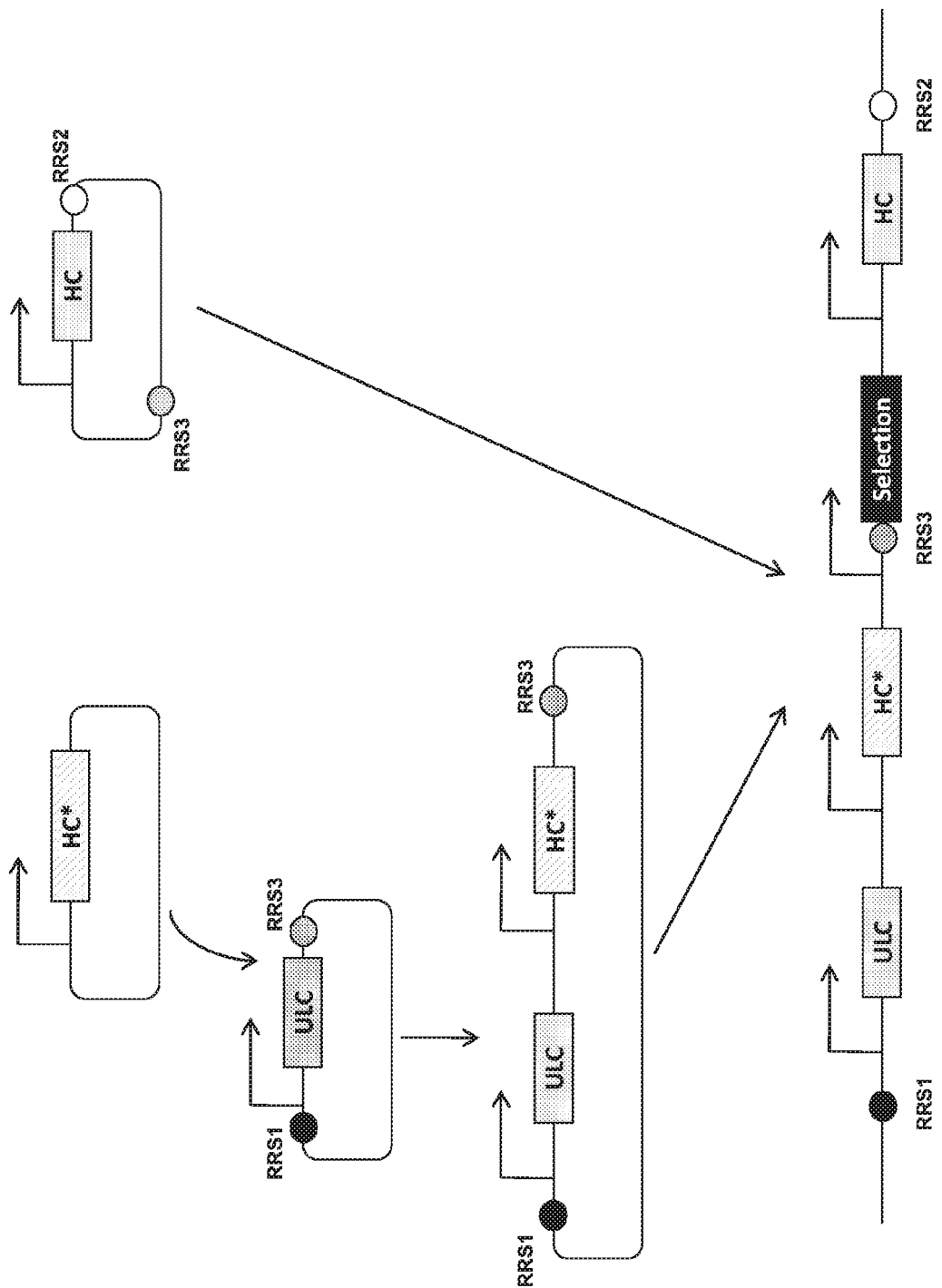
FIG. 2. An exemplary bispecific cloning strategy for integration within an expression enhancing locus. Utilizing a universal light chain (see, e.g. from a Humanized Universal Light Chain (ULC) VelocImmune® mouse, as described in WO 2013022782) having a 5' RRS (RRS1) allows efficient construction of new bispecific antibodies by inserting one heavy chain (HC*) flanked by a third RRS (RRS3) into pre-existing plasmids containing expression cassettes for the universal light chain. The second heavy chain (HC) is cloned into a second plasmid with RRS2 and RRS3 sites.
Figure 3:
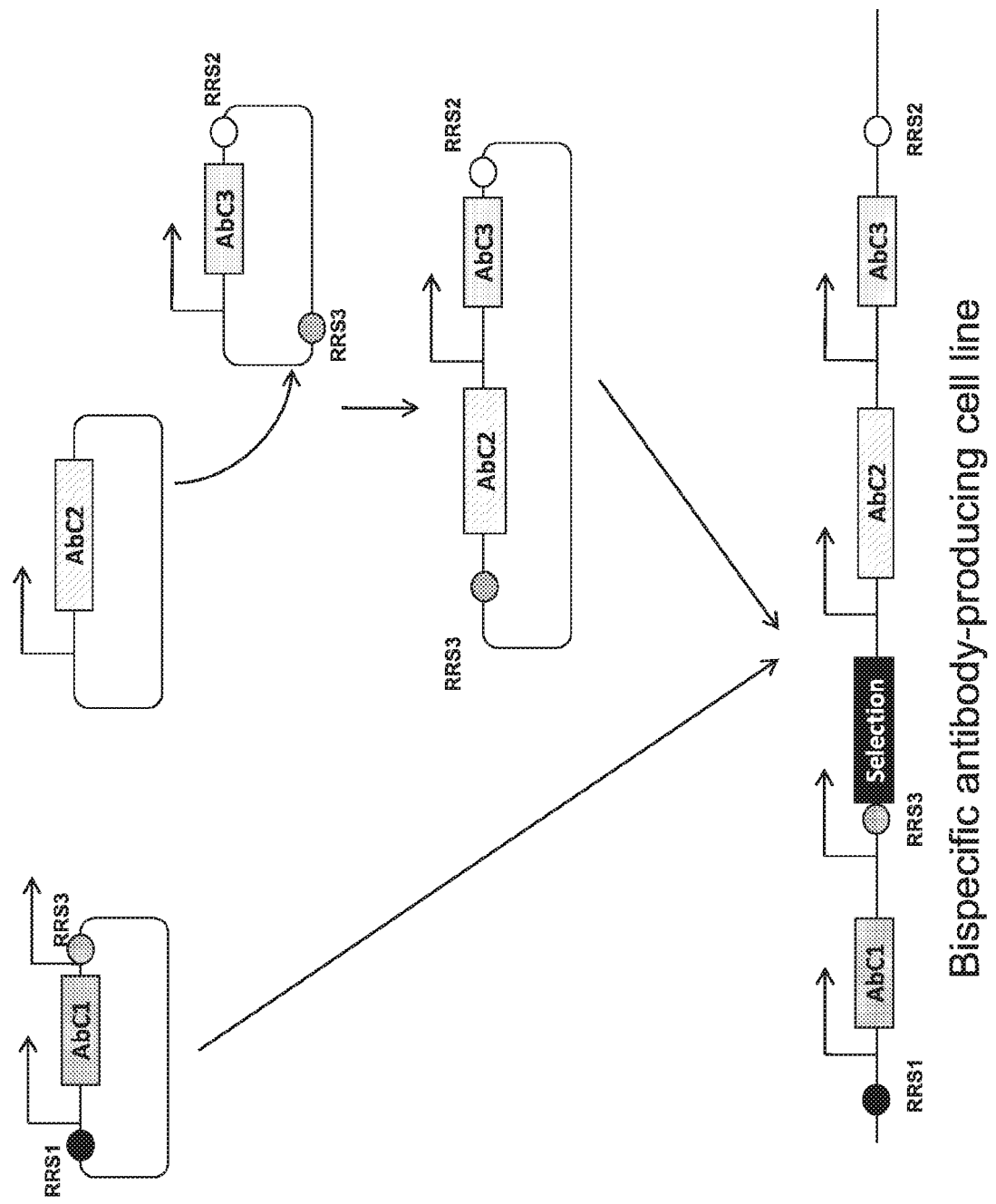
FIG. 3. An exemplary bispecific cloning strategy for integration within an expression enhancing locus. The three distinct antibody chains (AbC1, AbC2, and AbC3) of a bispecific antibody are first cloned into individual vectors. The AbC1 and AbC3 vectors each have RRS sites flanking the antibody expression cassette. Expression cassette for AbC2 is excised from the AbC2 plasmid and then subcloned into AbC3 expression plasmid, giving rise to a plasmid that contains, from 5' to 3', an RRS3 site, AbC2 expression cassette, AbC3 expression cassette, and an RRS2 site. This plasmid, together with the AbC1 plasmid and a recombinase, are introduced into host cells that harbor RRS1 and RRS2 in an expression enhancing locus. Bispecific antibody expression cell lines are isolated after recombinase-mediated cassette exchange.
Figure 4:
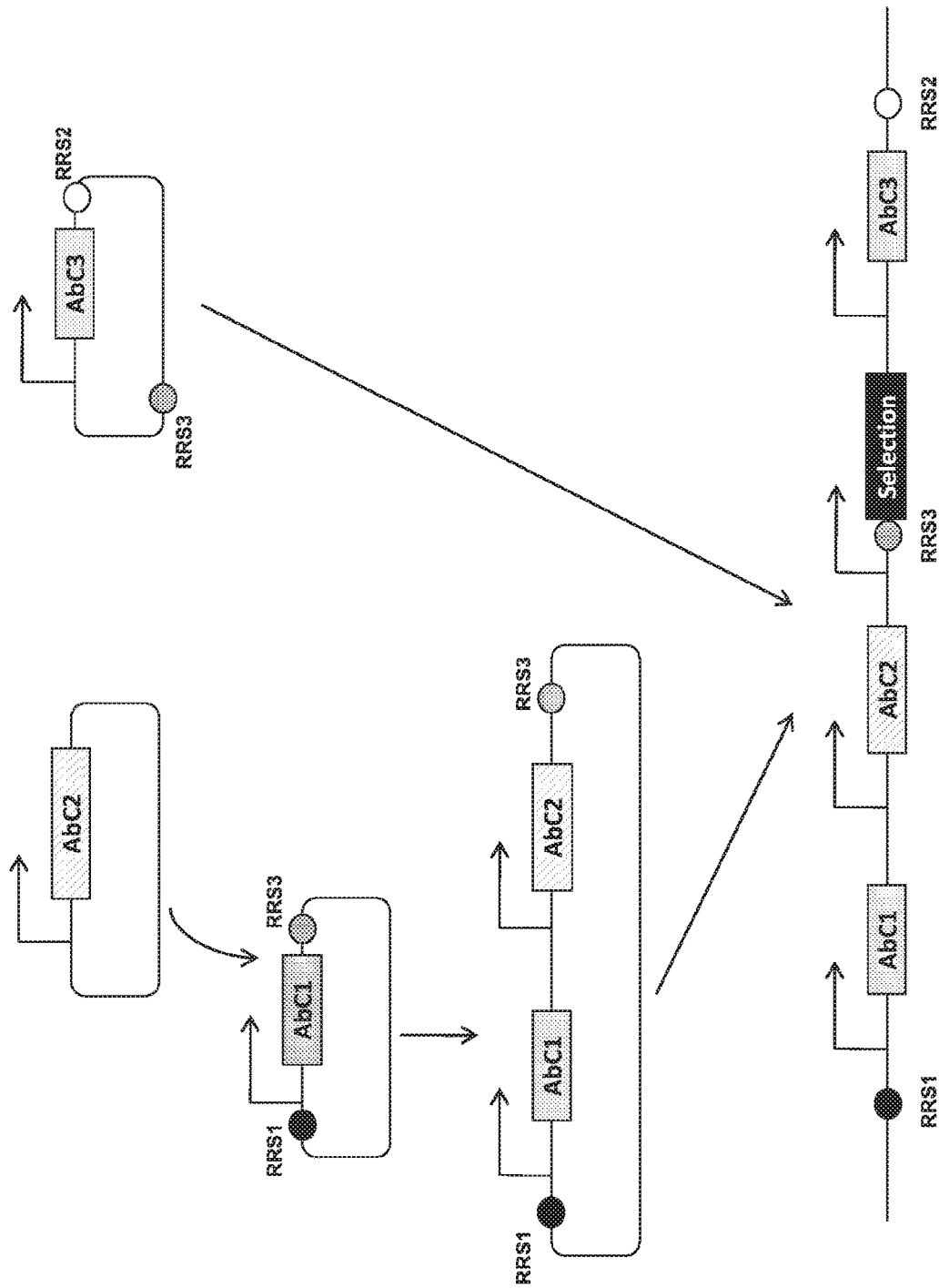
FIG. 4. An exemplary bispecific cloning strategy for integration within an expression enhancing locus. The three distinct antibody chains (AbC1, AbC2, and AbC3) of a bispecific antibody are first cloned into individual vectors. The AbC1 and AbC3 vectors each have RRS sites flanking the antibody expression cassette. Expression cassette for AbC2 is excised from the AbC2 plasmid and then subcloned into AbC1 expression plasmid, giving rise to a plasmid that contains, from 5' to 3', an RRS1 site, AbC1 expression cassette, AbC2 expression cassette, and an RRS3 site. This plasmid, together with the AbC3 plasmid and a recombinase, are introduced into host cells that harbor RRS1 and RRS2 in an expression enhancing locus. Bispecific antibody expression cell lines are isolated after recombinase-mediated cassette exchange FIG. 5. Expression of bispecific antibody from expression cassettes integrated at one genomic site (EESYR®). CHO cell lines RSX4189-1, RSX4187-1, RSX4191-1, RSX4188-1 were generated by recombinase-mediated cassette exchange at the EESYR® locus. The arrangements of expression cassettes for the three distinct antibody chains (AbC1, AbC2, and AbC3) of the bispecific Ab at the EESYR® locus are depicted on the left. The titers of each bispecific antibody in spent media of 4 day shaker flask cultures were determined by HPLC and are shown in the bar graph on the right.

The term "antibody", as used herein, includes immunoglobulin molecules comprised of four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3).

The phrase "antigen-binding protein" includes a protein that has at least one CDR and is capable of selectively recognizing an antigen, i.e., is capable of binding an antigen with a $K_D$ that is at least in the micromolar range. Therapeutic antigen-binding proteins (e.g., therapeutic antibodies) frequently require a $K_D$ that is in the nanomolar or the picomolar range. Typically, an antigen-binding protein includes two or more CDRs, e.g., 2, 3, 4, 5, or 6 CDRs. Examples of antigen binding proteins include antibodies, antigen-binding fragments of antibodies such as polypeptides containing the variable regions of heavy chains and light chains of an antibody (e.g., Fab fragment, F(ab')$_2$ fragment), and proteins containing the variable regions of heavy chains and light chains of an antibody and containing additional amino acids from the constant regions of heavy and/or light chains (such as one or more constant domains, i.e., one or more of CL, CH1, CH2, and CH3 domains).

The phrase "bispecific antigen-binding protein" includes antigen-binding proteins capable of selectively binding, or having different specificities to, two or more epitopes— either on two different molecules (e.g., antigens) or on the same molecule (e.g., on the same antigen). The antigen binding portion, or fragment antigen binding (Fab) portion of such protein renders specificity to a particular antigen, and is typically comprised of a heavy chain variable region and a light chain variable region of an immunoglobulin. In some circumstances, the heavy chain variable region and light chain variable region may not be a cognate pair, in other words, have a different binding specificities.

An example of a bispecific antigen-binding protein is a "bispecific antibody", which includes an antibody capable of selectively binding two or more epitopes. Bispecific antibodies generally comprise two different heavy chains, with each heavy chain specifically binding a different epitope— either on two different molecules (e.g., antigens) or on the same molecule (e.g., on the same antigen). If a bispecific antigen-binding protein is capable of selectively binding two different epitopes (a first epitope and a second epitope), the affinity of the variable region of the first heavy chain for the first epitope will generally be at least one to two or three or four orders of magnitude lower than the affinity of the variable region of the first heavy chain for the second epitope, and vice versa. Bispecific antigen-binding proteins such as bispecific antibodies can include the variable regions of heavy chains that recognize different epitopes of the same antigen. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding of one or both of the heavy chains to one or both epitopes. In one embodiment, an Fc domain includes at least CH2 and CH3. An Fc domain may include a hinge, a CH2 domain and CH3 domain.

One embodied bispecific format includes, a first heavy chain (HC), a second heavy chain which has a modified CH3 (HC*), and a common light chain (LC) (two copies of the same light chain). Another embodiment includes a first heavy chain (HC), a common LC and a HC-ScFv fusion polypeptide (wherein the second HC is fused to the N-terminus of the ScFv). Another embodiment includes a first HC, a cognate LC, an HC-ScFv fusion polypeptide (wherein the second HC is fused to the N-terminus of the ScFv). Another embodiment includes a first heavy chain (HC), a LC and an Fc domain. Another embodiment includes a first HC, an LC, an ScFv-Fc fusion polypeptide (wherein the Fc is fused to the C-terminus of the ScFv). Another embodiment includes a first HC, a common LC, and an Fc-ScFv fusion polypeptide (wherein the Fc is fused to the N-terminus of the ScFv). Another embodiment includes a first HC, a LC and an ScFv-HC (wherein the second HC is fused to the C-terminus of the ScFv).

In certain embodiments, one heavy chain (HC) may be native or "wild-type" sequence and the second heavy chain may be modified in the Fc domain. In other embodiments, one heavy chain (HC) may be native or "wild-type" sequence and the second heavy chain may be codon-modified.

The term "cell" includes any cell that is suitable for expressing a recombinant nucleic acid sequence, and has a locus that allows for stable integration and enhanced expression of an exogenous nucleic acid. Cells include mammalian cells, such as non-human animal cells, human cells, or cell fusions such as, for example, hybridomas or quadromas. In some embodiments, the cell is a human, monkey, ape, hamster, rat, or mouse cell. In some embodiments, the cell is a mammalian cell selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

"Cell density" refers to the number of cells per volume of sample, for example as number of total (viable and dead) cells per mL. The number of cells may be counted manually or by automation, such as with a flow cytometer. Automated cell counters have been adapted to count the number of viable or dead or both viable/dead cells using for example a standard tryptan blue uptake technique. The phrase "viable cell density" or "viable cell concentration" refers to the number of viable cells per volume of sample (also referred to as "viable cell count"). Any number of well-known manual or automated techniques may be used to determine cell density. Online biomass measurements of the culture may be measured, where the capacitance or optical density is correlated to the number of cells per volume. Final cell density in a cell culture, such as in a production culture, varies depending on the starting cell line, for example in the range of about 1.0 to $10\times10^6$ cells/mL. In some embodiments, final cell density reaches 1.0 to $10\times10^6$ cells/mL prior to harvest of protein of interest from a production cell culture. In other embodiments, final cell density reaches at least $5.0\times10^6$ cells/mL, at least $6\times10^6$ cells/mL, at least $7\times10^6$ cells/mL, at least $8\times10^6$ cells/mL, at least $9\times10^6$ cells/mL, or at least $10\times10^6$ cells/mL.

The term "codon modified" means that a protein-coding nucleotide sequence has been modified in one or more nucleotides, i.e., one or more codons, without changing the amino acids encoded by the codons, resulting in a codon-modified version of the nucleotide sequence. Codon modification of a nucleotide sequence can provide a convenient basis to differentiate a nucleotide sequence from its codon-modified version in a nucleic acid-based assay (e.g., a hybridization based assays, PCR, among others). In some instances, codons of a nucleotide sequence are modified to provide improved or optimized expression of the encoded protein in a host cell by employing codon optimization techniques well known in the art (Gustafsson, C., et al., 2004, *Trends in Biotechnology*, 22:346-353; Chung, B.K.-S., et al., 2013, *Journal of Biotechnology*, 167:326-333; Gustafsson, C., et al., 2012, *Protein Expr Purif,* 83(1): 37-46).

Sequence design software tools using such techniques are also well-known in the art, including but not limited to Codon optimizer (Fuglsang A. 2003, *Protein Expr Purif,* 31:247-249), Gene Designer (Villalobos A, et al., 2006, *BMC Bioinforma,* 7:285), and OPTIMIZER (Puigbò P, et al. 2007, *Nucleic Acids Research,* 35:W126-W131), among others.

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "expression enhancing locus" refers to a locus in the genome of a cell that contains a sequence or sequences and exhibits a higher level expression as compared to other regions or sequences in the genome when a suitable gene or construct is exogenously added (i.e., integrated) in or near the sequence or sequences, or "operably linked" to the sequence or sequences.

The term "enhanced" when used to describe enhanced expression includes an enhancement of at least about 1.5-fold to at least about 3-fold enhancement in expression over what is typically observed by random integration of an exogenous sequence into a genome or by integration at a different locus, for example, as compared to a pool of random integrants of a single copy of the same expression construct. Fold-expression enhancement observed employing the sequences of the invention is in comparison to an expression level of the same gene, measured under substantially the same conditions, in the absence of a sequence of the invention, for example in comparison to integration at another locus into the same species genome. Enhanced recombination efficiency includes an enhancement of the ability of a locus to recombine (for example, employing recombinase-recognition sites ("RRS")). Enhancement refers to an efficiency of recombination over random recombination for example, without employing recombinase-recognition sites or the like, which is typically 0.1%. A preferred enhanced recombination efficiency is about 10-fold over random, or about 1%. Unless specified, the claimed invention is not limited to a specific recombination efficiency. Enhanced expression loci typically support high productivity of the protein of interest by the host cell. Hence, enhanced expression includes high production of the protein of interest (elevated titer in grams of protein) per cell, rather than attaining high titers simply by high copy number of cells in culture. Specific productivity Qp (pg/cell/day, i.e. pcd) is considered a measure of sustainable productivity. Recombinant host cells exhibiting Qp greater than 5 pcd, or greater than 10 pcd, or greater than 15 pcd, or greater than 20 pcd, or greater than 25 pcd, or even greater than 30 pcd are desirable. Host cells with a gene of interest inserted into an expression-enhancing locus, or "hotspot", exhibit high specific productivity.

Where the phrase "exogenously added gene", "exogenously added nucleic acid", or simply "exogenous nucleic acid", is employed with reference to a locus of interest, the phrase refers to any DNA sequence or gene not present within the locus of interest as the locus is found in nature. For example, an "exogenous nucleic acid" within a CHO locus (e.g., a locus comprising a sequence of SEQ ID NO: 1 or SEQ ID NO: 2), can be a hamster gene not found within the particular CHO locus in nature (i.e., a hamster gene from another locus in the hamster genome), a gene from any other species (e.g., a human gene), a chimeric gene (e.g., human/mouse), or any other gene not found in nature to exist within the CHO locus of interest.

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. A typical heavy chain has, following the variable domain (from N-terminal to C-terminal), a CH1 domain, a hinge, a CH2 domain, and a CH3 domain. The term "a fragment of a heavy chain" or "a heavy chain fragment" (also referred to herein as "HCF"), includes a peptide of at least 10, 20, 30, 40, 50, 60, 70, 80, 90, 100 or more amino acids of a heavy chain, and may include one or more CDRs, one or more CDRs combined with one or more FRs, one or more of CH1, hinge, CH2, or CH3, the variable region, the constant region, fragments of the constant region (e.g. CH1, CH2, CH3), or combinations thereof. Examples of an HCF include VHs, and full or parts of Fc regions. The phrase "a nucleotide sequence encoding an HCF" includes nucleotide sequences encoding a polypeptide consisting of an HCF and nucleotide sequences encoding a polypeptide containing an HCF, e.g., polypeptides that may contain additional amino acids in addition to a specified HCF. For example, a nucleotide sequence encoding an HCF includes nucleotide sequences encoding polypeptides consisting of a VH, consisting of a VH linked to a CH3, consisting of a full heavy chain, among others.

A "homologous sequence" in the context of nucleic acid sequences refers to a sequence that is substantially homologous to a reference nucleic acid sequence. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding nucleotides are identical over a relevant stretch of residues. In some embodiments, the relevant stretch is a complete (i.e., full) sequence.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains that can be used with this invention include those, e.g., that do not selectively bind either the first or second epitope selectively bound by a bispecific antibody. Suitable light chains also include those that can bind or contribute to the binding of, one or both epitopes that are bound by the antigen-binding regions of an antibody. The term "a fragment of a light chain" or "a light chain fragment" (or "LCF") includes a peptide of at least 10, 20, 30, 40, 50, 60, 70, 80, 90, 100 or more amino acids of a light chain, and may include one or more CDRs, one or more CDRs combined with one or more FRs, the variable region, the constant region, fragments of the constant region, or combinations thereof. Examples of an LCF include VLs and full or parts of light chain constant regions ("CLs"). The phrase "a nucleotide sequence encoding an LCF" includes nucleotide sequences encoding a polypeptide consisting of an LCF and nucleotide sequences encoding a polypeptide containing an LCF, e.g., polypeptides that may contain additional amino acids in addition to a specified LCF. For example, a nucleotide sequence encoding an LCF includes nucleotide sequences encoding polypeptides consisting of a VL, or consisting of a full light chain, among others.

The phrase "operably linked" refers to linkage of nucleic acids or proteins in a manner that the linked molecules function as intended. DNA regions are operably linked when they are functionally related to each other. For example, a promoter is operably linked to a coding sequence if the promoter is capable of participating in the transcription of the sequence; a ribosome-binding site is operably linked to a coding sequence if it is positioned so as to permit translation. Generally, operably linked can include, but does not require, contiguity. In the case of sequences such as secretory leaders, contiguity and proper placement in a reading frame are typical features. An expression-enhancing sequence of the locus of interest is operably linked to a gene of interest (GOI) where it is functionally related to the GOI, for example, where its presence results in enhanced expression of the GOI.

"Percent identity", when describing a locus of interest, such as SEQ ID NO: 1 or SEQ ID NO: 2, or a fragment thereof, is meant to include homologous sequences that display the recited identity along regions of contiguous homology, but the presence of gaps, deletions, or insertions that have no homolog in the compared sequence are not taken into account in calculating percent identity.

As used herein, a "percent identity" determination between, e.g., SEQ ID NO: 1, or fragment thereof, with a species homolog, would not include a comparison of sequences where the species homolog has no homologous sequence to compare in an alignment (i.e., SEQ ID NO: 1 or the fragment thereof has an insertion at that point, or the species homolog has a gap or deletion, as the case may be). Thus, "percent identity" does not include penalties for gaps, deletions, and insertions.

"Recognition site" or "recognition sequence" is a specific DNA sequence recognized by a nuclease or other enzyme to bind and direct site-specific cleavage of the DNA backbone. Endonucleases cleave DNA within a DNA molecule. Recognition sites are also referred to in the art as recognition target sites.

"Recombinase recognition site" (or "RRS") is the specific DNA sequence recognized by a recombinase, such as Cre recombinase (Cre) or flippase (flp). Site-specific recombinases can perform DNA rearrangements, including deletions, inversions and translocations when one or more of their target recognition sequences are placed strategically into the genome of an organism. In one example, Cre specifically mediates recombination events at its DNA target recognition site loxP, which is composed of two 13-bp inverted repeats separated by an 8-bp spacer. More than one recombinase recognition site may be employed, for example, to facilitate a recombination-mediated exchange of DNA. Variants or mutants of recombinase recognition sites, for example lox sites, may also be employed (Araki, N. et al, 2002, *Nucleic Acids Research*, 30:19, e1103).

"Recombinase-mediated cassette exchange" or "RMCE" relates to a process for precisely replacing a genomic target cassette with a donor cassette. The molecular compositions typically provided in order to perform this process include 1) a genomic target cassette flanked both 5' and 3' by recognition target sites specific to a particular recombinase, 2) a donor cassette flanked by matching recognition target sites, and 3) the site-specific recombinase. Recombinase proteins are well known in the art (Turan, S. and Bode J., 2011, *FASEB J.*, 25, pp. 4088-4107) and enable precise cleavage of DNA within a specific recognition target site (sequence of DNA) without gain or loss of nucleotides. Common recombinase/site combinations include, but are not limited to, Cre/lox and Flp/frt. Commercially available kits also provide vectors containing the R4-attP site and a vector encoding the phiC31 integrase for RMCE. (See also, e.g. U.S. Published Application No. US20130004946.)

"Site-specific integration" or "targeted insertion" refers to gene targeting methods employed to direct insertion or integration of a gene or nucleic acid sequence to a specific location in the genome, i.e., to direct the DNA to a specific site between two nucleotides in a contiguous polynucleotide chain. Site-specific integration or targeted insertion may also be done for a particular nucleic acid that includes multiple expression units or cassettes, such as multiple genes, each having their own regulatory elements (such as promoters, enhancers, and/or transcriptional termination sequences). "Insertion" and "integration" are used interchangeably. It is understood that insertion of a gene or nucleic acid sequence (for example a nucleic acid sequence comprising an expression cassette) may result in (or may be engineered for) the replacement or deletion of one or more nucleic acids depending on the gene editing technique being utilized.

"Stable integration" means that an exogenous nucleic acid integrated in the genome of a host cell remains integrated for an extended period of time in cell culture, for example, at least 7 days, at least 10 days, at least 15 days, at least 20 days, at least 25 days, at least 30 days, at least 35 days, at least 40 days, at least 45 days, at least 50 days, at least 55 days, at least 60 days, or longer. It is understood that making bispecific antigen-binding proteins for manufacturing and purification at large-scale is a challenging task. Stability and clonality are essential to the reproducibility of any biomolecule, especially one to be used therapeutically. The stable clones expressing bispecific antibodies made by the methods of this disclosure provide a consistent and reproducible way to generate therapeutic biomolecules.

GENERAL DESCRIPTION

This disclosure provides for compositions and methods for improved expression of multiple polypeptides in a host cell particularly Chinese hamster (*Cricetulus griseus*) cell lines, by employing an expression-enhancing locus in the host cell. More specifically, the disclosure provides compositions and methods designed to integrate multiple exogenous nucleic acids that together encode a bispecific antigen-binding protein into a specific site within an expression-enhancing locus in a host cell such as a CHO cell. In particular, this disclosure provides cells containing multiple exogenous nucleic acids integrated at a specific site within an expression-enhancing locus wherein the multiple exogenous nucleic acids together encode a bispecific antigen-binding protein. This disclosure further provides nucleic acid vectors designed for site-specific integration of multiple exogenous nucleic acids into an expression-enhancing locus. This disclosure additionally provides systems that include a host cell containing two or more recombinase recognition sites (RRSs), and a set of vectors containing matching RRSs and multiple exogenous nucleic acids, for site-specific integration of the multiple exogenous nucleic acids from the vectors into an expression-enhancing locus. Further, this disclosure provides methods for making a bispecific antigen-binding protein using the cells, vectors and systems disclosed herein.

Cells Having Multiple Exogenous Nucleic Acids Integrated at a Specific Site within an Expression Enhancing Locus In one aspect, this disclosure provides a cell containing an exogenous nucleic acid sequence integrated at a specific site within an enhanced expression locus, wherein the exogenous nucleic acid sequence encodes a bispecific antigen-binding protein.

The cells provided herein are capable of producing a bispecific antigen-binding protein (e.g., a bispecific antibody) with high titers and/or high specific productivity (pg/cell/day). In some embodiments, a cell produces a bispecific antigen-binding protein at a titer of at least 5 mg/L, 10 mg/L, 15 mg/L, 20 mg/L, 25 mg/L, 30 mg/L, 35 mg/L, 40 mg/L, 45 mg/L, 50 mg/L, or greater. In some embodiments, a cell produces a bispecific antigen-binding protein at a ratio of the bispecific antigen-binding protein titer versus the total antigen-binding protein titer of at least 5%, 10%, 15%, 20%, 25%, 30%, 35%, 40%, 50%, or higher. In some embodiments, a cell that produces a bispecific antigen-binding protein has a specific productivity of at least 5, 6, 7, 8, 9, 10, 11, 12, 13, 14, 15 picogram/cell/day (pcd), or higher, determined based on total antigen-binding proteins (in pg) produced per cell per day.

The host cells comprising an exogenous nucleic acid sequence encoding a bispecific antigen-binding protein integrated at a specific site within an enhanced expression locus exhibit high cell density in production culture, e.g. 1 to $10 \times 10^6$ cells/mL. In other embodiments, the bispecific antigen-binding protein-encoding host cell has a final cell density of at least $5 \times 10^6$ cells/mL, $6 \times 10^6$ cells/mL, $7 \times 10^6$ cells/mL, $8 \times 10^6$ cells/mL, $9 \times 10^6$ cells/mL, or $10 \times 10^6$ cells/mL.

In some embodiments, the bispecific antigen-binding protein contains two HC fragments ("HCFs") having different antigen specificities and two LCFs. In instances where two VL regions are used, they can be the same or different. In specific embodiments, the two VL regions are the same, such as a common light chain.

In some embodiments, each of the two HCFs includes amino acids from a heavy chain constant region, such as CH1, CH2, or CH3. In specific embodiments, each of the two HCFs includes a CH3 domain. In particular embodiments, each of two HCFs include a constant region, i.e., a full constant region.

In some embodiments, each of the two HCFs include a VH, and the two VHs can be the same or different.

In some embodiments, the bispecific antigen-binding protein includes two heavy chains (i.e., two full heavy chains).

In some embodiments, each of the two LCFs includes a VL. In specific embodiments, each LCF consists of a VL region that is operably linked to an amino acid sequence that includes amino acids from a light chain constant region. In specific embodiments, each VL region is operably linked to a CL region, i.e., the bispecific antigen-binding protein includes a light chain (i.e., a full light chain).

In some embodiments, the exogenous nucleic acid sequence integrated within an enhanced expression locus includes a first exogenous nucleic acid containing a nucleotide sequence encoding a first LCF, a second exogenous nucleic acid containing a nucleotide sequence encoding a first HCF, and a third exogenous nucleic acid containing a nucleotide sequence encoding a second HCF.

In some embodiments, the nucleotide sequence encoding the first LCF can encode a light chain variable (VL) region sequence. In specific embodiments, the nucleotide sequence encoding the first VL region encode a first light chain.

In some embodiments, the nucleotide sequence encoding the first HCF encodes amino acids from a first heavy chain constant region, e.g., one or more of CH1, hinge, CH2, or CH3), and the nucleotide sequence encoding the second HCF encodes amino acids from a second heavy chain constant region. The amino acids from a first heavy chain constant region can be the same or different from the amino acids from a second heavy chain constant region. For example, the nucleotide sequence encoding the first HCF encodes a first CH3 domain, and the nucleotide sequence encoding the second HCF encodes a second CH3 domain, wherein the first and second CH3 domains can be the same, or different in one or more amino acid positions, as described herein below for bispecific antigen-binding proteins.

In some embodiments, the nucleotide sequence encoding the first HCF encodes a first VH, and the nucleotide sequence encoding the second HCF encodes a second VH.

In some embodiments, the nucleotide sequence encoding the first HCF encodes a first heavy chain, and the nucleotide sequence encoding the second HCF encodes a second heavy chain. The first and second heavy chains can have the same constant regions, or differ in one or more amino acids. Various examples of bispecific antigen-binding proteins that having different heavy chain constant domains (such as different CH3 domains) are further described herein below. Independent of the encoded amino acid sequences, the nucleotide sequences encoding amino acids from two heavy chain constant regions can differ in that one of the two coding nucleotide sequences can be codon modified, which provides a convenient basis to differentiate the two nucleotide sequences in a nucleic acid-based detection assay.

In some embodiments, each HCF- or LCF-coding nucleotide sequence is independently and operably linked to a transcriptional regulatory sequence that contains a promoter. By "independently", it means that each coding sequence is operably linked to a separate transcriptional regulatory sequence such as a promoter, so that the transcription of the coding sequences is under separate regulation and control. In some embodiments, the promoters directing transcription of the two HCF-containing polypeptides are the same. In some embodiments, the promoters directing transcription of the two HCF-containing polypeptides, as well as the promoter directing transcription of the LCF-containing polypeptide, are all the same, e.g., a CMV promoter. In some embodiments, each HCF- or LCF-coding nucleotide sequence is independently and operably linked to an inducible or repressible promoter. Inducible or repressible promoters allow production to occur, for example, only in production phase (fed-batch culture) and not during growth phase (seed train culture). Fine control of production (expression) of each gene product may be achieved by way of different promoters.

In one such example, cells are first engineered to express the tetracycline repressor protein (TetR) and each HCF- and LCF-coding nucleotide sequence is placed under transcriptional control of a promoter whose activity is regulated by TetR. Two tandem TetR operators (TetO) are placed immediately downstream of the CMV promoter. In some embodiments, each HCF- and/or LCF-coding nucleotide sequence is independently and operably linked to a promoter upstream of at least one TetR operator (TetO) or Arc operator (ArcO). In other embodiments, each HCF- and/or LCF-coding nucleotide sequence is independently and operably linked to a CMV/TetO or CMV/ArcO hybrid promoter. Additional suitable promoters are described herein below.

The relative positions of the multiple exogenous nucleic acids within the locus can vary. Without intending to be bound by any theory, it is believed that it is important to achieve balanced (i.e., comparable) expression levels of the two HCF-containing polypeptides. In some embodiments, the LCF encoding nucleic acid is located upstream relative to both HCF-encoding nucleic acids. In instances where the three promoters for directing the expression of the LCF-containing polypeptide and the two HCF-containing polypeptides are the same, a suitable arrangement can include, from 5' to 3', the nucleotide sequence encoding the LCF, the nucleotide sequence encoding the first HCF, an additional different promoter operably linked to a nucleotide sequence (such as a selectable marker gene), and the nucleotide sequence encoding the second HCF. Other suitable arrangements include, from 5' to 3', the nucleotide sequence encoding the LCF, an additional different promoter operably linked to a nucleotide sequence (such as a selectable marker gene), the nucleotide sequence encoding the first HCF, and the nucleotide sequence encoding the second HCF. Where the nucleotide sequences encoding a HCF encodes a constant region sequence, either the nucleotide sequence located upstream can encode a modified version of a constant region sequence (e.g., a modified CH3), or the nucleotide sequence located upstream can encode a modified version of a constant region sequence, with the other one encoding the unmodified version of the constant region sequence.

In some embodiments, the cell further contains one or more RRS, also integrated within the locus. In some embodiments, the cell includes a first and a second RRS different from each other and flanking an exogenous nucleic acid sequence, wherein the exogenous nucleic acid sequence in turn contains a first LCF-encoding nucleic acid, a first HCF-encoding nucleic acid, and a second HCF-encoding nucleic acid. In specific embodiments, the LCF encoding nucleic acid is located upstream relative to both HCF-encoding nucleic acids, and the cell includes a third RRS, located 3' relative to the first LCF-encoding nucleic acid, and 5' relative to one or both of the HCF-encoding exogenous nucleic acids, wherein the third RRS is different from the first and second RRSs. The third RRS can be engineered to be included in an intron of a gene which can be placed between any two of the HCF- or LCF-encoding sequences.

Bispecific Antigen-Binding Proteins

Bispecific antigen-binding proteins, such as bispecific antibodies, suitable for cloning and production in the cells, vectors, and systems described in this disclosure are not limited to any particular format of bispecific antigen-binding proteins.

In various embodiments, the bispecific antigen-binding protein includes two polypeptides, each containing an antigen-binding moeity (e.g., a VH region) and a CH3 domain, wherein the antigen-binding moeity of the two polypeptides have different antigen specificities, and wherein the two CH3 domains are heterodimeric in respect to each other in that one of the CH3 domains has been modified in at least one amino acid position to give rise to differential Protein A binding characteristics between the two polypeptides. See, e.g., the bispecific antibodies described in U.S. Pat. No. 8,586,713. In this way, a differential protein A isolation scheme can be employed to readily isolate the heterodimeric bispecific antigen-binding proteins from homodimers.

In some embodiments, the bispecific antigen-binding protein includes two heavy chains having different antigen specificities and differing in at least one amino acid position in the CH3 domain to give rise to differential Protein A binding characteristics between the two heavy chains.

In some embodiments, the two polypeptides contain CH3 domains of human IgG, wherein one of the two polypeptides contains the CH3 domain of a human IgG selected from IgG1, IgG2 and IgG4, and the other one of the two polypeptides contains a modified CH3 domain of a human IgG selected from IgG1, IgG2 and IgG4 wherein the modification reduces or eliminates the binding of the modified CH3 region to Protein A. In specific embodiments, one of the two polypeptides contains the CH3 domain of human IgG1, and the other one of the two polypeptides contains a modified CH3 domain of human IgG1 wherein the modification is selected from the group consisting of (i) 95R and (ii) 95R and 96F in the IMGT exon numbering system. In other specific embodiments, the modified CH3 domain comprises one to five additional modifications selected from the group consisting of 16E, 18M, 44S, 52N, 57M, and 82I in the IMGT exon numbering system.

In other various embodiments, the two polypeptides contain CH3 domains of mouse IgG, wherein one of the two polypeptides contains the CH3 domain of an unmodified mouse IgG, and the other one of the two polypeptides contains a modified CH3 domain of the mouse IgG wherein the modification reduces or eliminates the binding of the modified CH3 region to Protein A. In various embodiments, a mouse IgG CH3 region is modified to comprise particular amino acids at particular positions (EU numbering), selected from the group consisting of: 252T, 254T, and 256T; 252T, 254T, 256T, and 258K; 247P, 252T, 254T, 256T, and 258K; 435R and 436F; 252T, 254T, 256T, 435R, and 436F; 252T, 254T, 256T, 258K, 435R, and 436F; 24tP, 252T, 254T, 256T, 258K, 435R, and 436F; and, 435R. In a specific embodiment, a particular group of modifications is made, selected from the groups consisting of: M252T, S254T, S256T; M252T, S254T, S256T, I258K; I247P, M252T, S254T, S256T, I258K; H435R, H436F; M252T, S254T, S256T, H435R, H436F; M252T, S254T, S256T, I258K, H435R, H436F; I247P, M252T, S254T, S256T, I258K, H435R, H436F; and, H435R.

In various embodiments, a bispecific antigen-binding protein is a hybrid of a mouse and a rat monoclonal antibody or antigen-binding protein, e.g., a hybrid of mouse IgG2a and rat IgG2b. According to these embodiments, a bispecific antibody is composed of a heterodimer of the two antibodies comprising one heavy/light chain pair of each, associating via their Fc portions. The desired heterodimer can be easily purified from a mixture of two parental antibody homodimers and the bispecific heterodimer, because the binding properties of the bispecific antibody to Protein A are different from those of the parental antibodies: rat IgG2b does not bind to protein A, whereas the mouse IgG2a does. Consequently, the mouse-rat heterodimer binds to Protein A but elutes at a higher pH than the mouse IgG2a homodimer, and this makes selective purification of the bispecific heterodimer possible.

In other various embodiments, a bispecific antigen-binding protein is of a format that is referred to as "knobs-into-holes" in the art (see, e.g., U.S. Pat. No. 7,183,076). In these embodiments, the Fc portions of two antibodies are engineered to give one a protruding "knob", and the other a complementary "hole." When produced in the same cell, the heavy chains are said to preferentially form heterodimers rather than homodimers, by association of the engineered "knobs" with the engineered "holes."

In another embodiment, the first heavy chain and the second heavy chain comprises one or more amino acid modifications in the CH3 domain to enable interaction between two heavy chains. CH3-CH3 interface amino acid residues can be replaced with charged amino acid to provide electrostatically unfavorable homodimer formation. (See, e.g. PCT Publication No. WO2009089004; and European Publication No. EP1870459.)

In other embodiments, the first heavy chain comprises a CH3 domain of the isotype IgA and the second heavy chain comprises a CH3 domain of IgG (or vice versa) to promote preferential formation of heterodimers. (See e.g. PCT Publication No. WO2007110205.)

In other embodiments, various formats can be incorporated with immunoglobulin chains by engineering methods to foster formation of heterodimers, such as Fab-arm exchange (PCT Publication No. PCT Publication No. WO2008119353; PCT Publication No. WO2011131746), coiled-coil domain interaction (PCT Publication No. WO2011034605) or leucine zipper peptides (Kostelny, et al. *J. Immunol.* 1992, 148(5):1547-1553).

Immunoglobulin heavy chain variable regions that can be used to generate bispecific antigen-binding proteins can be generated using any method known in the art. For example, a first heavy chain comprises a variable region that is encoded by a nucleic acid that is derived from the genome of a mature B cell of a first animal that has been immunized with a first antigen, and the first heavy chain specifically recognizes the first antigen; and a second heavy chain comprises a variable region that is encoded by a nucleic acid that is derived from the genome of a mature B cell of a second animal that has been immunized with a second antigen, and the second heavy chain specifically recognizes the second antigen. Immunoglobulin heavy chain variable region sequences can also be obtained by any other method known in the art, e.g., by phage display. In other examples, nucleic acids encoding the heavy chain variable regions include those of antibodies that have been described or otherwise available in the art. In some embodiments, one of the two heavy chain coding sequences have been codon modified in order to provide a convenient basis to differentiate the two coding sequences in nucleic acid based assays.

Bispecific antibodies comprising two heavy chains that recognize two different epitopes (or two different antigens) are more easily isolated where they can pair with the same light chain (i.e., light chains having identical variable and constant domains). A variety of methods are known in the art for generating light chains that can pair with two heavy chains of differing specificity, while not interfering or not substantially interfering with the selectivity and/or affinity of the heavy chain variable domain with its target antigen, as described in e.g., U.S. Pat. No. 8,586,713 and the art disclosed therein.

The bispecific antigen-binding proteins can have a variety of dual antigen specificities and associated useful applications.

In some examples, bispecific antigen-binding proteins that comprise binding specificity toward a tumor antigen and a T-cell antigen can be made that target an antigen on a cell, e.g., CD20, and also target an antigen on a T-cell, e.g., a T cell receptor such as CD3. In this way, the bispecific antigen-binding protein targets both a cell of interest in a patient (e.g., B cell in a lymphoma patient, via CD20 binding) as well as a T-cell of the patient. The bispecific antigen-binding protein, in various embodiments, is designed so as to activate the T-cell upon binding a T cell receptor such as binding to CD3, thus coupling T-cell activation to a specific, selected tumor cell.

In the context of bispecific antigen-binding proteins wherein one moiety binds to CD3 and the other moiety binds to a target antigen, the target antigen can be a tumor-associated antigen. Non-limiting examples of specific tumor-associated antigens include, e.g., AFP, ALK, BAGE proteins, BIRC5 (survivin), BIRC7, f-catenin, brc-abl, BRCA1, BCMA, BORIS, CA9, carbonic anhydrase IX, caspase-8, CALR, CCR5, CD19, CD20(MS4A1), CD22, CD30, CD40, CDK4, CEA, CLEC-12, CTLA4, cyclin-B1, CYP 1B, EGFR, EGFRvII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, TAG-72, TGF-β, TMPRSS2, Thompson-nouvelle antigen (Tn), TRP-1, TRP-2, tyrosinase, and uroplakin-3.

In some embodiments, the bispecific antigen-binding protein is selected from the group consisting of an anti-CD3× anti-CD20 bispecific antibody (as described in U.S. Pat. Appln. Pub. Nos. US2014/0088295A1 and US20150266966A1, herein incorporated by reference), an anti-CD3×anti-Mucin 16 bispecific antibody (e.g., an anti-CD3×anti-Muc16 bispecific antibody), and an anti-CD3× anti-Prostate-specific membrane antigen bispecific antibody (e.g., an anti-CD3×anti-PSMA bispecific antibody). In other embodiments, the bispecific antigen-binding protein comprises one moiety that binds CD3. Exemplified anti-CD3 antibody moieties are described in U.S. Pat. Appln. Pub. Nos. US2014/0088295A1 and US20150266966A1, and in International Publication No. WO 2017/053856 published on Mar. 30, 2017, all of which are incorporated herein by reference). In still other embodiments, the bispecific antigen-binding protein comprises one moiety that binds to CD3 and one moiety that binds to BCMA, CD19, CD20, CD28, CLEC-12, Her2, HLA protein, MAGE protein, Muc16, PSMA, or Steap-2.

In the context of bispecific antigen-binding proteins wherein one moiety binds to a T cell receptor such as binds to CD3 and the other moiety binds a target antigen, the target antigen can be an infectious disease-associated antigen. Non-limiting examples of infectious disease-associated antigens include, e.g., an antigen that is expressed on the surface of a virus particle, or preferentially expressed on a cell that is infected with a virus, wherein the virus is selected from the group consisting of HIV, hepatitis (A, B or C), herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillomavirus, molluscum virus, poliovirus, rabies virus, JC virus, and arboviral encephalitis virus. Alternatively, the target antigen can be an antigen that is expressed on the surface of a bacterium, or preferentially expressed on a cell that is infected with a bacterium, wherein the bacterium is selected from the group consisting of chlamydia, rickettsia, mycobacteria, staphylococci, streptococci, pneumonococci, meningococci, gonococci, klebsiella, proteus, serratia, pseudomonas, legionella, diphtheria, salmonella, bacilli, cholera, tetanus, botulism, anthrax, plague, leptospira, and Lyme disease bacteria. In certain embodiments, the target antigen is an antigen that is expressed on the surface of a fungus, or preferentially expressed on a cell that is infected with a fungus, wherein the fungus is selected from the group consisting of *Candida* (*albicans, krusei, glabrata, tropicalis,* etc.), *Crytococcus neoformans, Aspergillus* (*fumigatus, niger,* etc.), *Mucorales* (*mucor, absidia, rhizopus,* etc.), *Sporothrix schenkii, Blastomyces dermatitidis, Paracoccidioides brasiliensis, Coccidioides immitis,* and *Histoplasma capsulatum*. In certain embodiments, the target antigen is an antigen that is expressed on the surface of a parasite, or preferentially expressed on a cell that is infected with a parasite, wherein the parasite is selected from the group consisting of *Entamoeba histolytica, Balantidium coli, Naegleria fowleri, Acanthamoeba* sp.*, Giardia lambia, Cryptosporidium* sp.*, Pneumocystis carinii, Plasmodium vivax, Babesia microti, Trypanosoma brucei, Trypanosoma cruzi, Leishmania donovani, Toxoplasma gondii, Nippostrongylus brasiliensis, Taenia crassiceps,* and *Brugia malayi*. Non-limiting examples of specific pathogen-associated antigens include, e.g., HIV gp120, HIV CD4, hepatitis B glucoprotein L, hepatitis B glucoprotein M, hepatitis B glucoprotein S, hepatitis C E1, hepatitis C E2, hepatocyte-specific protein, herpes simplex virus gB, cytomegalovirus gB, and HTLV envelope protein.

Bispecific binding proteins that comprise two binding moieties that are each directed to a binding partner (i.e., each directed to a different target) on the surface of the same cell can also be made. This design is particularly suited to targeting specific cells or cell types that express both targets on the surface of the same cell. Although targets might appear individually on other cells, the binding moieties of these binding proteins are selected such that each binding moiety binds its target with a relatively low affinity (e.g., low micromolar, or high nanomolar—e.g., over a hundred nanomolar KD, e.g., 500, 600, 700, 800 nanomolar). In this way, prolonged target binding is favored only in situations where the two targets are in proximity on the same cell.

Bispecific binding proteins that comprise two binding moieties that bind the same target, each at a different epitope of the same target, can be made. This design is particularly suited for maximizing the probability of successfully blocking a target with binding protein. Multiple extracellular loops, e.g., of a transmembrane channel or a cell surface receptor, can be targeted by the same bispecific binding molecule.

Bispecific binding proteins that comprise two binding moieties that cluster and activate negative regulators of immune signaling to result in immune suppression can be made. Repression in cis can be achieved where the targets are on the same cell; repression in trans can be achieved where the targets are on different cells. Repression in cis, e.g., can be achieved with a bispecific binding protein having an anti-IgGRIIb binding moiety and an anti-FelD1 binding moiety, such that the IgGRIIb is clustered only in the presence of FelD1, in order to down-regulate an immune response to FelD1). Repression in trans, e.g., can be achieved with a bispecific binding protein having an anti-BTLA binding moiety and a binding moiety that specifically binds a tissue-specific antigen of interest, such that clustering of the inhibitory BTLA molecule occurs only in the selected target tissue, which potentially addresses autoimmune diseases.

Bispecific binding proteins that activate multi-component receptors can be made. In this design, two binding moieties directed to two components of a receptor bind, cross-link the receptor, and activate signaling from the receptor. This can be done, e.g., using a bispecific binding protein with a binding moiety that binds IFNAR1 and a binding moiety that binds IFNAR2, where binding cross-links the receptor. Such a bispecific binding protein can provide an alternative to interferon treatment.

Bispecific binding proteins that transport binding moieties across a semi-permeable barrier, e.g., the blood-brain barrier, can be made. In this design, one binding moiety binds a target that can transit a particular selective barrier, the other binding moiety targets a molecule with a therapeutic activity, wherein the target molecule with therapeutic activity cannot normally traverse the barrier. This kind of bispecific binding protein is useful for bringing therapeutics to tissues that the therapeutic would not otherwise reach. Some examples include targeting the pGR receptor to transport a therapeutic into the gut or lung, or targeting the transferrin receptor to transport a therapeutic across the blood-brain barrier.

Bispecific binding proteins that transport binding moieties into specific cells or cell types can be made. In this design, one binding moiety targets a cell surface protein (e.g., a receptor) that is readily internalized into the cell. The other binding moiety targets an intracellular protein, where binding of the intracellular protein results in a therapeutic effect.

Bispecific binding proteins that bind a surface receptor of a phagocytic immune cell and a surface molecule of an infectious pathogen (e.g., a yeast or bacterium), to bring the infectious pathogen in the vicinity of a phagocytic immune cell to facilitate phagocytosis of the pathogen. An example of such a design would be a bispecific antibody that targets a CD64 or CD89 molecule and also a pathogen.

Bispecific binding proteins that have an antibody variable region as one binding moiety and a non-Ig moiety as a second binding moiety. The antibody variable region achieves targeting, whereas the non-Ig moiety is an effector or a toxin linked to an Fc. In this way, the ligand (e.g., an effector or toxin) is delivered to the target bound by the antibody variable region.

Bispecific binding proteins that have two moieties each bound to an Ig region (e.g., an Ig sequence containing a CH2 and CH3 region) such that any two protein moieties can be brought in each other's vicinity in the context of the Fc. Examples of this design include traps, e.g., homo- or heterodimeric trap molecules.

Expression-Enhancing Loci

Expression-enhancing loci suitable for use in this invention include for example, a locus that comprises a nucleotide sequence having substantial homology to SEQ ID NO: 1 as described in U.S. Pat. No. 8,389,239 (also referred to herein as the "EESYR® locus"), a locus that comprises a nucleotide sequence having substantial homology to SEQ ID NO: 2 or SEQ ID NO: 3 as described in U.S. application Ser. No. 14/919,300 (also referred to herein as "the YARS locus"), and other expression-enhancing loci and sequences documented in the art (e.g., US 20150167020A1, and U.S. Pat. No. 6,800,457).

In some embodiments, the expression-enhancing locus that is used in this invention is selected from a locus that comprises a nucleotide sequence having substantial homology to SEQ ID NO: 1, or a locus that comprises a nucleotide sequence having substantial homology to SEQ ID NO: 2 or SEQ ID NO: 3. These loci contain sequences that not only provide for enhanced expression of genes integrated in operable linkage to the sequences (i.e., within the sequences or within close proximity to the sequences), but also exhibit greater recombination efficiency and improved integration stability, as compared to other sequences in the genome.

SEQ ID NO: 1, SEQ ID NO: 2 and SEQ ID NO: 3 have been identified from CHO cells. Other mammalian species (such as, for example, humans or mice), were found to have limited homology to the identified expression-enhancing region; however, homologous sequences may be found in cell lines derived from other tissue types of Cricetulus griseus, or other homologous species, and can be isolated by techniques that are well-known in the art. For example, one may identify other homologous sequences by cross-species hybridization or PCR-based techniques. In addition, changes can be made in the nucleotide sequence set forth in SEQ ID NO: 1, SEQ ID NO: 2, or SEQ ID NO: 3 by site-directed or random mutagenesis techniques that are well known in the art. The resulting sequence variants can then be tested for expression-enhancing activity. DNAs that are at least about 90% identical in nucleic acid identity to SEQ ID NO: 1, SEQ ID NO: 2, or SEQ ID NO: 3 having expression-enhancing activity are isolatable by routine experimentation, and are expected to exhibit expression-enhancing activity.

The integration site, the site or nucleotide position of insertion of one or more exogenous nucleic acids, can be at any position that is within or adjacent to any of the expression enhancing sequences (such as SEQ ID NO: 1, SEQ ID NO: 2 or SEQ ID NO: 3). Whether a specific chromosomal location within or adjacent to the locus of interest supports stable integration and efficient transcription of an integrated exogenous gene can be determined in accordance with standard procedures well known in the art, e.g., as described U.S. Pat. No. 8,389,239 and U.S. application Ser. No. 14/919,300.

The integration sites considered herein are located within the expression enhancing sequences, or within close proximity to the sequences, e.g., less than about 1 kb, 500 base pairs (bp), 250 bp, 100 bp, 50 bp, 25 bp, 10 bp, or less than about 5 bp upstream (5') or downstream (3') with respect to the location of an expression enhancing sequence on the chromosomal DNA. In still some other embodiments, the employed integration site is located at about 1000, 2500, 5000 or more base pairs upstream (5') or downstream (3') with respect to the location of an expression enhancing sequence on the chromosomal DNA.

It is understood in the art that large genomic regions, such as scaffold/matrix attachment regions, are employed for efficient replication and transcription of chromosomal DNA. A scaffold/matrix attachment region (S/MAR), also known as called scaffold-attachment region (SAR), or matrix-associated or matrix attachment region (MAR), is a eukaryotic genomic DNA region where the nuclear matrix attaches. Without being bound by any one theory, S/MARs typically map to non-coding regions, separate a given transcriptional region (e.g. chromatin domain) from its neighbors, and also provide platforms for the machinery and/or binding of factors that enable transcription, such as recognition sites for DNAses or polymerases. Some S/MARs have been characterized at about 14-20 kb in length (Klar, et al. 2005, *Gene* 364:79-89). As such, integration of genes at an expression enhancing locus (e.g., within or near SEQ ID NO: 1, SEQ ID NO: 2, or SEQ ID NO:3) is expected to confer enhanced expression. In some embodiments, the host cells comprising an exogenous nucleic acid sequence encoding a bispecific antigen-binding protein integrated at a specific site within an enhanced expression locus exhibits high specific productivity. In other embodiments, the bispecific antigen-binding protein-encoding host cell has a specific productivity of at least 5, 6, 7, 8, 9, 10, 1, 12, 13, 14, 15, 20, 25, or 30 picogram/cell/day (pcd).

In some embodiments, the integration site is within a locus that comprises the nucleotide sequence of SEQ ID NO: 1. In specific embodiments, the integration site is within, or within close proximity to, the nucleotide sequence of SEQ ID NO: 1. In particular embodiments, the integration site is at a position within SEQ ID NO: 1 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In other embodiments, the integration site is in a sequence that is selected from the group consisting of nucleotides 5,000-7,400, 5,000-6,500, 6,400-7,400 of SEQ ID NO: 1; and nucleotides 6,400-6,500 of SEQ ID NO: 1. In a specific embodiment, the integration site before, after, or within the "act" triplet of nucleotides 6471 to 6473 of SEQ ID NO: 1.

In some embodiments, the integration site is within a locus that comprises the nucleotide sequence of SEQ ID NO: 2 or SEQ ID NO:3. In specific embodiments, the integration site is within, or within close proximity to, the nucleotide sequence of SEQ ID NO: 2. In particular embodiments, the integration site is within, or within close proximity to, the nucleotide sequence of SEQ ID NO: 3. In some embodiments, the integration site is within nucleotides 1990-1991, 1991-1992, 1992-1993, 1993-1994, 1995-1996, 1996-1997, 1997-1998, 1999-2000, 2001-2002, 2002-2003, 2003-2004, 2004-2005, 2005-2006, 2006-2007, 2007-2008, 2008-2009, 2009-2010, 2010-2011, 2011-2012, 2012-2013, 2013-2014, 2014-2015, 2015-2016, 2016-2017, 2017-2018, 2018-2019, 2019-2020, 2020-2021 or 2021-2022 of SEQ ID NO: 3. In specific embodiments, the integration is at or within nucleotides 2001-2022 of SEQ ID NO: 3. In some embodiments, the exogenous nucleic acid is inserted at or within nucleotides 2001-2002 or nucleotides 2021-2022 of SEQ ID NO: 3 and nucleotides 2002-2021 of SEQ ID NO: 3 are deleted, as a result of the insertion.

Site-Specific Integration into an Expression-Enhancing Locus

Integration of multiple exogenous nucleic acids into an expression-enhancing locus in a site-specific manner, i.e., into one specific site within an expression-enhancing locus as disclosed herein, can be achieved in several ways including, e.g., by homologous recombination, and recombinase mediated cassette exchange, as described in the art (see e.g., U.S. Pat. No. 8,389,239 and the art disclosed therein).

In some embodiments, cells are provided that contain at least two, i.e., two or more, different recombinase recognition sequences (RRS) within an expression-enhancing locus convenient for integrating an nucleic acid sequence containing multiple exogenous nucleic acids or genes of interest. Such cells can be obtained by introducing an exogenous nucleic acid sequence containing two or more RRS into a desirable locus by various means including homologous recombination, as described hereinbelow and in the art, e.g., U.S. Pat. No. 8,389,239 and the art disclosed therein.

In specific embodiments, cells are provided that contain more than two different recombinase recognition sequences (RRS) within an expression-enhancing locus convenient for integrating multiple exogenous nucleic acids. In particular embodiments, cells are provided that contain three different recombinase recognition sequences (RRS) within an expression-enhancing locus which can mediate integration of two separate exogenous nucleic acids, for example, wherein the 5' RRS and the middle RRS in the genome match the 5' RRS and the 3' RRS flanking the first exogenous nucleic acid to be integrated, and the middle RRS and 3' RRS in the genome match the 5' RRS and the 3' RRS flanking the second exogenous nucleic acid to be integrated.

Suitable RRSs can be selected from the group comprising LoxP, Lox511, Lox5171, Lox2272, Lox2372, Loxm2, Lox-FAS, Lox71, Lox66 and the mutants thereof, where the site specific recombinase is Cre recombinase or its derivative is used to achieve recombinase-mediated cassette exchange (RMCE). In other examples, suitable RRS can be selected from the group comprising FRT, F3, F5, FRT mutant-10, FRT mutant+10 and the mutants thereof, and in this scenario, the site-specific recombinase Flp recombinase or its derivative is used to achieve RMCE. In yet another example, RRSs can be selected from the group comprising attB, attP and the mutants thereof, and in this case where the site-specific recombinase phiC31 integrase or its derivative is used to achieve RMCE.

In other embodiments, native cells are modified by a homologous recombination technique to integrate a nucleic acid sequence containing multiple exogenous nucleic acids into a specific site within an expression-enhancing locus.

For homologous recombination, homologous polynucleotide molecules (i.e. homologous arms) line up and exchange a stretch of their sequences. A transgene can be introduced during this exchange if the transgene is flanked by homologous genomic sequences. In one example, a recombinase recognition site can be introduced into the host cell genome at the integration sites via homologous recombination. In other examples, a nucleic acid sequence containing multiple exogenous nucleic acids, e.g., multiple nucleic acids that together encode a bispecific antigen-binding protein, wherein the nucleic sequence is flanked by sequences homologous to the sequences at the target locus ("homologous arms"), is inserted into the host genome.

Homologous recombination in eukaryotic cells can be facilitated by introducing a break in the chromosomal DNA at the integration site. This may be accomplished by targeting certain nucleases to the specific site of integration. DNA-binding proteins that recognize DNA sequences at the target locus are known in the art. Gene targeting vectors are also employed to facilitate homologous recombination.

Gene targeting vector construction and nuclease selection to achieve homologous recombination are within the skill of the artisan to whom this invention pertains. In some examples, zinc finger nucleases (ZFNs), which have a modular structure and contain individual zinc finger domains, recognize a particular 3-nucleotide sequence in the target sequence (e.g. site of targeted integration). Some embodiments can utilize ZFNs with a combination of individual zinc finger domains targeting multiple target sequences. Transcription activator-like (TAL) effector nucleases (TALENs) may also be employed for site-specific genome editing. TAL effector protein DNA-binding domain is typically utilized in combination with a non-specific cleavage domain of a restriction nuclease, such as FokI. In some embodiments, a fusion protein comprising a TAL effector protein DNA-binding domain and a restriction nuclease cleavage domain is employed to recognize and cleave DNA at a target sequence within the locus of the invention (Boch J et al., 2009 *Science* 326:1509-1512). RNA-guided endonucleases (RGENs) are programmable genome engineering tools that were developed from bacterial adaptive immune machinery. In this system—the clustered regularly interspaced short palindromic repeats (CRISPR)/CRISPR-associated (Cas) immune response— the protein Cas9 forms a sequence-specific endonuclease when complexed with two RNAs, one of which guides target selection. RGENs consist of components (Cas9 and tracrRNA) and a target-specific CRISPR RNA (crRNA). Both the efficiency of DNA target cleavage and the location of the cleavage sites vary based on the position of a protospacer adjacent motif (PAM), an additional requirement for target recognition (Chen, H. et al, *J. Biol. Chem.* published online Mar. 14, 2014, as Manuscript M113.539726). Sequences unique for a specific targeting locus (such as SEQ ID NO: 1, SEQ ID NO: 2 or SEQ ID NO: 3) can be identified by aligning many of these sequences to the CHO genome which can reveal potential off-target sites with 16-17 base pair match.

In some embodiments, a targeting vector carrying a nucleic acid of interest (e.g., a nucleic acid containing one or more RRSs optionally flanking one or more selectable marker gene, or a nucleic acid containing multiple exogenous nucleic acids which together encode a bispecific antigen-binding protein), flanked by 5' and 3' homology arms, is introduced into a cell with one or more additional vectors or mRNA. In one embodiment, the one or more additional vectors or mRNA contain a nucleotide sequence encoding a site-specific nuclease, including but not limited to a zinc finger nuclease (ZFN), a ZFN dimer, a transcription activator-like effector nuclease (TALEN), a TAL effector domain fusion protein, and an RNA-guided DNA endonuclease. In certain embodiments, the one or more vectors or mRNA include a first vector comprising a guide RNA, a tracrRNA and a nucleotide sequence encoding a Cas enzyme, and a second vector comprising a donor (exogenous) nucleotide sequence. Such donor sequence contains a nucleotide sequence coding for the gene of interest, or the recognition sequence, or the gene cassette comprising any one of these exogenous elements intended for targeted insertion. Where mRNA is used, the mRNA can be transfected into the cell by means of common transfection methods known to the skilled person and may encode an enzyme, for example a transposase or endonuclease. Although an mRNA introduced into the cells may be transient and does not integrate into the genome, the mRNA may carry an exogenous nucleic acid necessary or beneficial for the integration to take place. In some instances, mRNA is chosen in order to eliminate any risk of long-lasting side effects of an accessory polynucleotide, where only short-term expression is required to achieve the desired integration of a nucleic acid.

Vectors for Site Specific Integration

Nucleic acid vectors are provided herein for introducing exogenous nucleic acids into an expression enhancing locus via site-specific integration. Suitable vectors include vectors designed to contain an exogenous nucleic sequence flanked by RRSs for integration via RMCE, and vectors designed to contain an exogenous nucleic sequence of interest flanked by homology arms for integration via homologous recombination.

In various embodiments, vectors are provided to achieve site-specific integration via RMCE. In some embodiments, vectors are designed to achieve simultaneous integration of multiple nucleic acids into a target locus. In contrast to sequential integration, simultaneous integration permits efficiency and rapid isolation of desirable clones that produce a bispecific antigen-binding protein.

In some embodiments, a set of vector is provided and includes two or more vectors, each vector containing at least two RRSs flanking one or more nucleic acids, wherein the nucleic acids in the vectors of the set together encoding a bispecific antigen binding protein.

In one embodiment, a set of vectors include a first vector comprising from 5' to 3': a first RRS, a first nucleic acid comprising a nucleotide sequence encoding a first LCF, and a third RRS; a second vector comprising from 5' to 3', the third RRS, a second nucleic acid comprising a nucleotide sequence encoding a first HCF, a second RRS; wherein either the first or the second nucleic acid further comprises a nucleotide sequence encoding a second HCF; and wherein the first and second HCFs, and the first LCF, encode regions (e.g., variable regions) of a bispecific antigen-binding protein. In some embodiments, the nucleotide sequence encoding the second HCF is included in the first nucleic acid on the first vector (i.e., first LCF and second HCF on one vector), optionally placed, e.g., downstream of the nucleotide sequence encoding the first LCF; and in other embodiments, the nucleotide sequence encoding the second HCF is included in the second nucleic acid on the second vector (first HCF and second HCF on one vector).

The nucleotide sequences encoding HCF can encode amino acids, e.g., amino acids or domain(s) from a constant region, or encode an entire constant region. In specific embodiments, a nucleotide sequences encoding an HCF or LCF can encode one or more constant domains, such as CL, CH1, hinge CH2, CH3, or combinations thereof. In certain embodiments, a nucleotide sequence encoding a HCF can encode a CH3 domain. For example, the nucleotide sequence encoding the first HCF can encode a first CH3 domain, and the nucleotide sequence encoding the second HCF can encode a second CH3 domain. The first and second CH3 domains can be the same, or differ in at least one amino acid. The differences in the CH3 domains or in the constant regions can take any of the formats for bispecific antigen-binding proteins described herein, e.g., differences that result in different Protein A binding characteristics, electrostatic steering, or in a "knob-and-hole" format. Independent of any amino acid sequence differences, the two HCF-coding nucleotide sequences can also differ in that one of the two nucleotide sequences has been codon modified.

In some embodiments, each HCF-coding nucleotide sequence is independently and operably linked to a transcriptional regulatory sequence including e.g., a promoter. In some embodiments, the promoters directing transcription of the two HCF-containing polypeptides are the same. In some embodiments, the promoters directing transcription of the two HCF-containing polypeptides, as well as the promoter directing transcription of the LCF-containing polypeptide, are all the same (e.g., a CMV promoter). In some embodiments, each HCF- or LCF-coding nucleotide sequence is independently and operably linked to an inducible or repressible promoter. Inducible or repressible promoters allow production to occur, for example, only in production phase (fed-batch culture) and not during growth phase (seed train culture). Inducible or repressible promoters also allow for differential expression of one or more genes of interest. In some embodiments, each HCF- and/or LCF-coding nucleotide sequence is independently and operably linked to a promoter upstream of at least one TetR operator (TetO) or Arc operator (ArcO). In still other embodiments, each HCF- and/or LCF-coding nucleotide sequence is independently and operably linked to a CMV/TetO or CMV/ArcO hybrid promoter. Examples of hybrid promoters (also referred to as regulatory fusion proteins) may be found in International Publication No. WO03101189A1, published Dec. 11, 2003 (herein incorporated by reference).

In some embodiments, the first nucleic acid in the first vector further comprises a 5' portion of a selectable marker gene, located at 5' to the third RRS in the first vector; and the second nucleic acid further comprises the remaining 3' portion of the selectable marker gene, located 3' to the third RRS in the second vector. In these embodiments, the first, second and third RRSs mediate site-specific integration of the first and second nucleic acids, which results in the joining of the 5' portion and the 3' portion of the selectable marker gene in properly and simultaneously integrated clones for convenient selection. In certain embodiments, the third RRS in the first vector is designed to be within a 5' portion of an intron of the selectable marker gene; and the third RRS in the second vector is designed to be within a 3' portion of an intron of the selectable marker gene. In still other embodiments, the third RRS in the first vector is designed to be between a promoter and the selectable marker gene to which it is operably linked (but it is separated from on the other vector); the third RRS in the first vector is designed to be 3' of a promoter; and the third RRS in the second vector is designed to be 5' of the selectable marker gene.

The set of vectors described above can include more than two vectors. For example, in addition to the two vectors described above, the set can include a third vector comprising at least two RRSs flanking a nucleotide sequence encoding a second LCF. The set of can also include a vector encoding one or more recombinases that recognizes the RRSs.

In other embodiments, vectors are provided to achieve site-specific integration via homologous recombination. In some examples, the polynucleotide sequence to be integrated into a host genome can be a DNA sequence, such as a RRS, or multiple RRSs flanking one or more selectable marker genes, for generating cells having one or more RRSs integrated in a desired locus for subsequent integration of nucleic acids encoding a bispecific antigen-binding protein. In other examples, the polynucleotide sequence to be integrated into the host genome includes multiple nucleic acids that together encode a bispecific antigen-binding protein. For example, the polynucleotide sequence includes nucleic acids encoding two different heavy chains and the common light chain of a bispecific antibody. In some embodiments, the multiple nucleic acids that together encode a bispecific antigen-binding protein are each independently (i.e., separately) operably linked to regulatory sequences (such as a promoter, enhancer, a transcriptional termination sequence, or a combination thereof)—that is, the regulatory sequences (such as promoters) for each of the multiple nucleic acids are separate, which can be the same or different (i.e., containing the same or different nucleotide sequences). In instances where a nucleic acid among the multiple nucleic acids include multiple coding sequences, each coding sequence or each nucleotide sequence coding for the N-terminal portion of a polypeptide, is independently and operably linked to their own regulatory sequences (such as promoter).

It is well within the skill of the artisan to select sequences homologous to sequences within an expression enhancing locus and include the selected sequences as homology arms in a targeting vector. In some embodiments, the vector or construct comprises a first homologous arm and a second homologous arm, wherein the first and second homologous arms combined comprise a targeted sequence which replaces an endogenous sequence within the locus. In other embodiments, the first and second homologous arms comprise a targeted sequence which integrates or inserts within an endogenous sequence within the locus. In some embodiments, the homology arms contain a nucleotide sequence homologous to a nucleotide sequence present in SEQ ID NO: 1, SEQ ID NO: 2, or SEQ ID NO: 3. In specific embodiments, the vector contains a 5' homology arm having the nucleotide sequence corresponding to nucleotides 1001-2001 of SEQ ID NO: 3, and a 3' homology arm having the nucleotide corresponding to nucleotides 2022-3022 of SEQ ID NO: 3. Homologous arms, for example a first homologous arm (also called 5' homology arm) and a second homologous arm (also called 3' homology arm) are homologous to a targeted sequence within the locus. The homologous arms from 5' to 3' may expand a region or targeted sequence within the locus that comprises at least 1 kb, or at least about 2 kb, or at least about 3 kb, or at least about 4 kb, or at least 5 kb, or at least about 10 kb. In other embodiments, the total number of nucleotides of a targeted sequence selected for a first and second homologous arm comprises at least 1 kb, or at least about 2 kb, or at least about 3 kb, or at least about 4 kb, or at least 5 kb, or at least about 10 kb. In some instances, the distance between the 5' homology arm and the 3' homology arm (homologous to the targeted sequence) comprises at least 5 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, or at least 1 kb, or at least about 2 kb, or at least about 3 kb, or at least about 4 kb, or at least 5 kb, or at least about 10 kb. In instances where nucleotides 1001-2001 and 2022-3022 of SEQ ID NO: 3 are chosen as 5' and 3' homology arms, the distance between the two homology arms can be 20 nucleotides (corresponding to nucleotides 2002-2021 of SEQ ID NO: 3); and such homology arms can mediate integration of an exogenous nucleic acid sequence within a locus comprising SEQ ID NO: 3, e.g., within nucleotides 1990-2021 or 2002-2021 of SEQ ID NO: 3, and a simultaneous deletion of nucleotides 2002-2021 of SEQ ID NO: 3.

The vectors disclosed herein for introducing exogenous nucleic acids for site-specific integration into an expression enhancing locus can include additional genes and sequences for directing the expression of exogenous nucleic acids of interest and encoded polypeptides and for the selection and identification of cells into which the exogenous nucleic acids of interest have successfully integrated. Such additional sequences include, for example, transcriptional and translational regulatory sequences, selectable marker genes, and the like, also described hereinbelow.

Regulatory Sequences

The vectors disclosed herein for introducing exogenous nucleic acids into an expression enhancing locus in a site-specific manner, and the cells obtained as a result of site-specific integration, can include regulator sequences for directing the expression of exogenous nucleic acids of interest and encoded polypeptides. Regulatory sequences include transcriptional promoters, enhancers, sequences encoding suitable mRNA ribosomal binding sites, and sequences that control the termination of transcription and translation. Transcriptional and translational control sequences may be provided by viral sources. For example, commonly used promoters and enhancers are derived from viruses such as polyoma, adenovirus 2, simian virus 40 (SV40), mouse or human cytomegalovirus (CMV), CMV immediate early (CMV-IE) or CMV major IE (CMV-MIE) promoter, as well as RSV, SV40 late promoter, SL3-3, MMTV, ubiquitin (Ubi), ubiquitin C (UbC), and HIV LTR promoters. Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the proteins of interest are to be expressed. DNA sequences derived from the SV40 viral genome, for example, the SV40 origin, early and late promoter, enhancer, splice, and polyadenylation sites may be used to provide other genetic elements useful for expression of a exogenous DNA sequence. Early and late promoters are particularly useful because both are obtained easily from the SV40 virus as a fragment that also comprises the SV40 viral origin of replication (Fiers et al., *Nature* 273:113, 1978). Smaller or larger SV40 fragments may also be used. Typically, the approximately 250 bp sequence extending from the Hind III site toward the BglI site located in the SV40 origin of replication is included. Inducible promoters (induced by a chemical compound, cofactor, regulatory protein, for example) can be used and are particularly useful for allowing the production of antigen binding proteins to occur only in production phase (fed-batch culture) and not during growth phase (seed train culture). Examples of inducible or repressible promoters include alcohol dehydrogenase I gene promoters, tetracycline-responsive promoter systems, glucocorticoid receptor promoters, estrogen receptor promoter, ecdysone receptor promoters, metallothionein-based promoters, and T7-polymerase based promoters. Sequences suitable for the expression of multiple transcripts via a bicistronic vector have been described previously (Kim S. K. and Wold B. J., *Cell* 42:129, 1985) and can be used this invention. Examples of suitable strategies for multicistronic expression of proteins include the use of a 2A peptide (Szymczak et al., *Expert Opin Biol Ther* 5: 627-638 (2005)) and the use of an internal ribosome entry site ("IRES"), both well known in the art. Other types of expression vectors will also be useful, for example, those described in U.S. Pat. No. 4,634,665 (Axel et al.) and U.S. Pat. No. 4,656,134 (Ringold et al.).

Selectable Markers

The vectors disclosed herein for introducing exogenous nucleic acids into an expression enhancing locus in a site-specific manner, and the cells obtained as a result of site-specific integration, can include one or more selectable markers genes.

In some embodiments, a selectable marker gene confers drug resistance, such as, for example, those described in Table 1 of Kaufman, R. J. (1988) *Meth. Enzymology* 185: 537, and include DHFR-MTX resistance, P-glycoprotein and multiple drug resistance (MDR)-various lipophilic cytotoxic agents (e.g., adriamycin, colchicine, vincristine), and adenosine deaminase (ADA)-Xyl-A or adenosine and 2'-deoxycoformycin. Other dominant selectable markers include microbially derived antibiotic resistance genes, for example neomycin, kanamycin or hygromycin resistance. Several suitable selection systems exist for mammalian hosts (Sambrook supra, pgs 16.9-16.15). Co-transfection protocols employing two dominant selectable markers have also been described (Okayama and Berg, *Mol. Cell Biol* 5:1136, 1985).

1 In other embodiments, a selectable marker gene encodes a polypeptide that provides or is capable of generating a detectable signal for the recognition of gene cassettes that have or have not been successfully inserted and/or replaced, as the case may be. Suitable examples include a fluorescent marker or protein, an enzyme that catalyzes a chemical reaction that generates a detectable signal, among others. Examples of fluorescent markers are well-known in the art, including, but not limited to *Discosoma* coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein (e.g. mKate, mKate2, mPlum, mRaspberry or E2-crimson. See also, e.g., Nagai, T., et al. 2002 *Nature Biotechnology* 20:87-90; Heim, R. et al. 23 Feb. 1995 *Nature* 373:663-664; and Strack, R. L. et al. 2009 *Biochemistry* 48:8279-81.

Systems for Making Bispecifc Antigen-Binding Proteins

In a further aspect, this disclosure provides systems that include a combination of a cell and one or more vectors, and that can be utilized to make cells having integrated within an expression enhancing locus exogenous nucleic acids that together encode a bispecific antigen binding protein. The systems can be provided in the form of a kit, for example.

In some embodiments, a system is designed to permit efficient vector construction and simultaneous integration of multiple exogenous nucleic acids via RMCE into a specific site within an enhanced expression locus. Simultaneous integration permits rapid isolation of desirable clones, and the use of one enhanced expression locus is also important for creation of a stable cell line.

In some embodiments, a system is provided that includes any one of the set of vectors described above designed to integrate multiple exogenous nucleic acids via RMCE, and a cell containing RRSs that are integrated at a specific site within an enhanced expression locus and that match the RRS in the set of vectors. For example, a system includes a cell and a set for vectors, wherein the cell contains, integrated within an enhanced expression locus of its genome from 5' to 3': a first RRS, a first exogenous nucleic acid, a second RRS, a second exogenous nucleic acid, and a third RRS, wherein the three RRSs are different from one another, wherein the set of vectors includes a first vector comprising from 5' to 3', the first RRS, a first nucleic acid comprising a nucleotide sequence encoding a first LCF (e.g., a first VL), and the second RRS; a second vector comprising the second RRS, a second nucleic acid comprising a nucleotide sequence encoding a first HCF (e.g., a first VH), and the third RRS; and wherein either the first nucleic acid or the second nucleic acid further comprises a nucleotide sequence encoding a second HCF (e.g., a second VH). Upon introduction of the vectors into the cell, the first and second nucleic acids in the vectors integrate into the enhanced expression locus through recombination mediated by the first, second and third RRSs. To facilitate screening of transfectants having nucleic acids properly integrated from the vectors into the locus, the first exogenous nucleic acid in the cell of the system can include a first selectable marker gene, and the second exogenous nucleic acid in the cell can include a second selectable marker gene, wherein the first and second selectable marker genes are different from each other, and are also different from any selectable marker gene provided by the vectors; and in specific embodiments, the first and second selectable marker genes encode fluorescent proteins (which can provide negative selection), and the first and second nucleic acids on the vectors provide an additional selectable marker gene in a split format to provide positive selection. Negative selection alone can provide rapid clone isolation, although the efficiency of isolating clones with intended recombination may be limited (about 1%). Negative selection coupled with positive selection (a new fluorescence, or a resistance to a drug or antibiotic) can significantly improve the efficiency of isolation of positive clones (to about 80%).

The systems can include additional components, reagents, or information, for examples, protocols for introducing the vector(s) in a system into the cell of the system by transfection. Non-limiting transfection methods include chemical-based transfection methods include the use of liposomes; nanoparticles; calcium phosphate (Graham et al. (1973) *Virology* 52 (2): 456-67, Bacchetti et al. (1977) *Proc Natl Acad Sci USA* 74 (4): 1590-4 and, Kriegler, M (1991) Transfer and Expression: A Laboratory Manual. New York: W. H. Freeman and Company. pp. 96-97); dendrimers; or cationic polymers such as DEAE-dextran or polyethylenimine. Non chemical methods include electroporation; sonoporation; and optical transfection. Particle-based transfection include the use of a gene gun, magnet assisted transfection (Bertram, J. (2006) *Current Pharmaceutical Biotechnology* 7, 277-28). Viral methods can also be used for transfection. mRNA delivery includes methods using TransMessenger™ and TransIT® (Bire et al. *BMC Biotechnology* 2013, 13:75). One commonly used method of introducing heterologous DNA into a cell is calcium phosphate precipitation, for example, as described by Wigler et al. (*Proc. Natl. Acad. Sci. USA* 77:3567, 1980). Polyethylene-induced fusion of bacterial protoplasts with mammalian cells (Schaffner et al., (1980) *Proc. Natl. Acad. Sci. USA* 77:2163) is another useful method of introducing heterologous DNA. Electroporation can also be used to introduce DNA directly into the cytoplasm of a host cell, for example, as described by Potter et al. (*Proc. Natl. Acad. Sci. USA* 81:7161, 1988) or Shigekawa et al. (BioTechniques 6:742, 1988). Other reagents useful for introducing heterologous DNA into a mammalian cell have been described, such as Lipofectin™ Reagent and Lipofectamine™ Reagent (Gibco BRL, Gaithersburg, Md.). Both of these commercially available reagents are used to form lipid-nucleic acid complexes (or liposomes) which, when applied to cultured cells, facilitate uptake of the nucleic acid into the cells.

Methods for Making Bispecific Antigen-Binding Proteins

This disclosure also provides methods of making bispecific antigen-binding proteins. By utilizing the present methods, a bispecific antigen-binding protein (e.g., a bispecific antibody) can be produced at high titers and/or high specific productivity (pg/cell/day). In some embodiments, a bispecific antigen-binding protein is produced at a titer of at least 5 mg/L, 10 mg/L, 15 mg/L, 20 mg/L, 25 mg/L, 30 mg/L, 35 mg/L, 40 mg/L, 45 mg/L, 50 mg/L, or greater. In some embodiments, a bispecific antigen-binding protein is produced at a ratio of the bispecific antigen-binding protein titer versus the total antigen-binding protein titer of at least 5%, 10%, 15%, 20%, 25%, 30%, 35%, 40%, 50%, or higher. In some embodiments, a bispecific antigen-binding protein is produced at a specific productivity of at least 5, 6, 7, 8, 9, 10, 11, 12, 13, 14, 15 picogram/cell/day, or higher, determined based on total antigen-binding proteins (in pg) produced per cell per day.

In one embodiment, the method utilizes a system disclosed herein and introduces the vectors in the system into the cell of the system by transfection. Transfected cells where the exogenous nucleic acids have been properly integrated into a target enhanced expression locus of the cell through RMCE can be screened and identified. The two HCF-containing polypeptides and at least one LCF-containing polypeptide can be expressed from the integrated nucleic acids, and the bispecific antigen-binding protein containing all three polypeptides can be obtained from the identified transfected cell, and purified using known methods.

In some embodiments, a method includes (i) providing a system that includes a cell and a set for vectors, wherein the cell contains, integrated within an enhanced expression locus of its genome from 5' to 3': a first RRS, a first exogenous nucleic acid, a second RRS, a second exogenous nucleic acid, and a third RRS, wherein the three RRSs are different from one another, wherein the set of vectors includes a first vector comprising from 5' to 3', the first RRS, a first nucleic acid comprising a nucleotide sequence encoding a first LCF (e.g., a first VL), and the second RRS; a second vector comprising the second RRS, a second nucleic acid comprising a nucleotide sequence encoding a first HCF (e.g., a first VH), and the third RRS; and wherein either the first nucleic acid or the second nucleic acid further comprises a nucleotide sequence encoding a second HCF (e.g., a second VH); (ii) introducing the vectors simultaneously into the cell; and (iii) screening for transformed cells in which the first and second nucleic acids in the vectors have simultaneously integrated into the enhanced expression locus through recombination mediated by the first, second and third RRSs.

In a specific embodiment of the method, to facilitate screening of transformants having nucleic acids properly integrated from the vectors into the locus, the first exogenous nucleic acid in the cell of the system can include a first selectable marker gene, and the second exogenous nucleic acid in the cell can include a second selectable marker gene, wherein the first and second selectable marker genes are different from each other, and the first and second nucleic acids on the vectors together encode an additional selectable marker in a split format where a complete sequence encoding the additional selectable marker gene is provided following simultaneous integration. Screening for transformants can be conducted to select against the first and second selectable markers (negative selection), and for the additional selectable marker (positive selection).

In another embodiment, the method simply utilizes a cell having an exogenous nucleic acid sequence integrated at a specific site within an enhanced expression locus of the cell, wherein the exogenous nucleic acid sequence encodes a bispecific antigen-binding protein, and expresses the bispecific antigen-binding protein from the cell. The cloned expression cassette in contiguous within the specific integration site.

The present description is further illustrated by the following examples, which should not be construed as limiting in any way. The contents of all cited references (including literature references, issued patents, and published patent applications as cited throughout this application) are hereby expressly incorporated by reference.

EXAMPLES

Example 1: Cloning of Bispecific Antibody Expression Plasmids

The heavy and light chain components of bispecific antibodies may be cloned from hybridoma cells, B cells, plasma cells, or recombinant antibody gene libraries using methods known in the art. For example, antibodies may be cloned from hybridoma or B cells by five prime RACE PCR, or PCR using primers against leader peptides, framework 1 sequences, framework 4 sequences, or constant region sequences. Alternatively, antibody genes or mRNAs in antibody-expressing cells may be sequenced by next-generation sequencing and subsequently identified through bioinformatics. It is also feasible to sequence antibody proteins and clone the corresponding antibody genes by synthetic DNA technology. Recombinant antibody libraries, such as yeast or phage libraries, are also sources of antibody genes.

Figure 5:
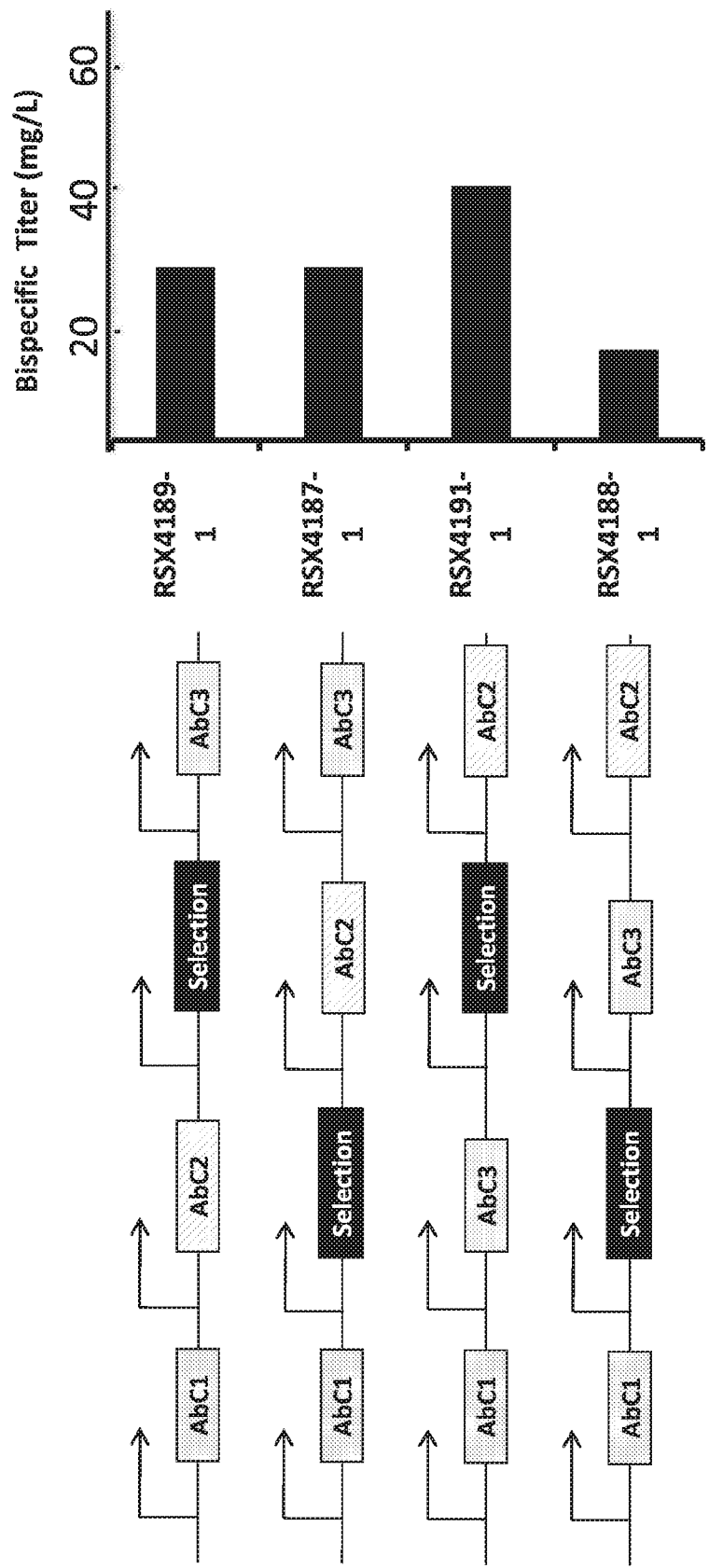

The CHO expression cell lines RSX4189-1, RSX4187-1, RSX4191-1, and RSX4188-1 each produce a bispecific antibody comprised of three distinct polypeptides: AbC1, AbC2, and AbC3 (FIG. 5). To generate plasmids for construction of RSX4189-1, the AbC1 plasmid was linearized by digestion with Mfe I, which was 3' to the AbC1 gene. The AbC2 expression cassette excised from the AbC2 plasmid by Mfe I digestion was ligated to the Mfe I site of the linearized AbC1 plasmid. The ligation products were transformed into DH10B *E. coli*. After transformation and growth in Ampicillin-containing LB media, individual *E. coli* colonies were analyzed for harboring the desired plasmid containing AbC1 and AbC2 genes. Sequences of maxi-prep DNA for the AbC3 plasmid and the AbC1-AbC2 dual expression plasmid were confirmed by Sanger sequencing. These two plasmids, together with the Cre expression plasmid pRG858, were transfected into EESYR® host cells harboring RRS1 and RRS3 sites at the EESYR® locus using lipofectamine. The transfected cells were selected with antibiotics for 12 days, and recombinant cells were subsequently pooled as RSX4189-1.

To generate plasmids for construction of RSX4187-1, the AbC3 expression cassette flanked by Mlu I and Nhe I sites was cloned into the Mlu I and Spe I sites in the AbC2 plasmid, 3' to the AbC2 gene. The combined AbC2-AbC3 plasmid, the AbC1 plasmid, and the Cre plasmid pRG858 was co-transfected into EESYR® host cells using lipofectamine. The cells that had undergone RMCE were pooled as RSX4187-1.

To generate plasmids for construction of RSX4191-1, the AbC3 expression cassette was cloned into the Mfe I site in the AbC1 plasmid, 3' to the AbC1 gene. The combined AbC1-AbC3 plasmid, the AbC2 plasmid, and the Cre plasmid pRG858 was co-transfected into EESYR® host cells using lipofectamine. The cells that had undergone RMCE were pooled as RSX4191-1.

To generate plasmids for construction of RSX4188-1, the AbC2 expression cassette flanked by Mlu I and Nhe I sites was cloned into the Mlu I and Spe I sites in the AbC3 plasmid, 3' to the AbC3 gene. The combined AbC3-AbC2 plasmid, the AbC1 plasmid, and the Cre plasmid pRG858 was co-transfected into EESYR® host cells using lipofectamine. The cells that had undergone RMCE were pooled as RSX4188-1.

Example 2: Expression of Bispecific Antibody from the EESYR® Locus

The bispecific antibody expression cell lines RSX4189-1, RSX4187-1, RSX4191-1, and RSX4188-1 were cultured in suspension in serum-free medium. To quantitate their bispecific antibody expression levels, the cell numbers of the cultures were counted on a Guava flow cytometer and fresh shaker flask cultures containing 2 million cells per ml medium were started. 4 days later, the spent media were harvested after centrifugation to remove the cells. The bispecific antibody titers were determined using a protein A HPLC assay that was specific to the bispecific antibody. The titers of the bispecific antibody protein expressed from RSX4189-1, RSX4187-1, RSX4191-1, and RSX4188-1 were 37.8 mg/L, 40.5 mg/L, 48.3 mg/L, and 21.8 mg/L, respectively. The total titer of all antibody proteins (including the bispecific antibody protein and the monospecific antibody proteins) expressed from these cell lines, and the ratio of the bispecific antibody protein titer versus the total antibody protein titer, are shown in the table below.

| AbPID/RSX | BispecificTiter (mg/L) | Total Titer (mg/L) | % Bispecific |
|---|---|---|---|
| RSX4187-1 | 40.5 | 211.7 | 19.10% |
| RSX4188-1 | 21.8 | 218.3 | 10.00% |
| RSX4189-1 | 37.8 | 199.5 | 19.00% |
| RSX419-1 | 48.3 | 172.9 | 27.90% |

What is claimed is:

1. A cell comprising an exogenous nucleic acid sequence integrated at a specific site within an enhanced expression locus,
wherein the exogenous nucleic acid sequence comprises a first exogenous nucleic acid comprising a nucleotide sequence encoding a first light chain fragment (LCF), a second exogenous nucleic acid comprising a nucleotide sequence encoding a first heavy chain fragment (HCF), and a third exogenous nucleic acid comprising a nucleotide sequence encoding a second HCF;
wherein the nucleotide sequence encoding the first LCF is operably linked to a first promoter, the nucleotide sequence encoding the first HCF is operably linked to a second promoter, and the nucleotide sequence encoding the second HCF is operably linked to a third promoter;
wherein the first and second HCFs, and the first LCF, are fragments of a bispecific antigen-binding protein a bispecific antibody.

2. A set of vectors, comprising
a first vector comprising from 5' to 3': a first recombinase recognition site (RRS), a first nucleic acid comprising a nucleotide sequence encoding a first LCF, and a third RRS;
a second vector comprising from 5' to 3', said third RRS, a second nucleic acid comprising a nucleotide sequence encoding a first HCF, a second RRS;
wherein either the first or the second nucleic acid further comprises a nucleotide sequence encoding a second HCF;
wherein the first and second HCFs, and the first LCF, are fragments of a bispecific antigen-binding protein; and
wherein the nucleotide sequence encoding the first LCF is operably linked to a first promoter, the nucleotide sequence encoding the first HCF is operably linked to a second promoter, and the nucleotide sequence encoding the second HCF is operably linked to a third promoter.

3. The set of vectors of claim 2, wherein the nucleotide sequence encoding the second HCF is included in the first nucleic acid.

4. The set of vectors of claim 2, wherein the nucleotide sequence encoding the second HCF is included in the second nucleic acid.

5. The set of vectors of claim 2, wherein the nucleotide sequence encoding the first HCF encodes a first CH3 domain, and the nucleotide sequence encoding the second HCF encodes a second CH3 domain.

6. The set of vectors of claim 5, wherein the first and second CH3 domains differ in at least one amino acid position, or wherein the nucleotide sequences encoding the first and second CH3 domains differ from each other in that one of the nucleotide sequences has been codon modified.

7. The set of vectors of claim 2, wherein the nucleotide sequence encoding the first HCF encodes a first heavy chain variable region (VH), and the nucleotide sequence encoding the second HCF encodes a second heavy chain VH.

8. The set of vectors of claim 2, wherein the nucleotide sequence encoding the first LCF encodes a first light chain variable region (VL).

9. The set of vectors of claim 2, wherein the first nucleic acid further comprises a second promoter located 5' to the third RRS in the first vector; and the second nucleic acid further comprises a selectable marker gene, located 3' to the third RRS in the second vector.

10. The set of vectors of the claim 2, wherein
the first vector comprising from 5' to 3', the first RRS, the first nucleic acid, and the third RRS; and
the second vector comprising 5' to 3', the third RRS, the second nucleic acid wherein the second nucleic acid comprises the nucleotide sequence encoding a first HCF and the nucleotide sequence encoding a second HCF.

11. The set of vectors of the claim 2, wherein
the first vector comprising from 5' to 3', the first RRS, the first nucleic acid wherein the first nucleic acid comprises the nucleotide sequence encoding the first LCF and the nucleotide sequence encoding the second HCF, and the third RRS; and
the second vector comprising 5' to 3', the third RRS, the second nucleic acid wherein the second nucleic acid comprises a nucleotide sequence encoding the first HCF.

12. The set of vectors of claim 2, further comprising a third vector comprising one or more RRSs and a nucleotide sequence encoding a second LCF.

13. The set of vectors of claim 2, further comprising a third vector encoding one or more recombinases that recognize the RRSs.

14. A system comprising a cell and a set of vectors,
wherein the cell comprises, integrated within an enhanced expression locus of its genome from 5' to 3': a first recombinase recognition site (RRS), a first exogenous nucleic acid, a third RRS, a second exogenous nucleic acid, and a second RRS, wherein the three RRSs are different from one another;

wherein the set of vectors comprises
a first vector comprising from 5' to 3', the first RRS, a first nucleic acid comprising a nucleotide sequence encoding a first light chain fragment (LCF), and the third RRS;
a second vector comprising the third RRS, a second nucleic acid comprising a nucleotide sequence encoding a first heavy chain fragment (HCF), and the second RRS; and
wherein either the first nucleic acid or the second nucleic acid further comprises a nucleotide sequence encoding a second HCF;
wherein the nucleotide sequence encoding the first LCF is operably linked to a first promoter, the nucleotide sequence encoding the first HCF is operably linked to a second promoter, and the nucleotide sequence encoding the second HCF is operably linked to a third promoter; and
wherein upon introduction of the vectors into the cell, the first and second nucleic acids in the vectors integrate into the enhanced expression locus through recombination mediated by the first, second and third RRSs.

15. The system of claim 14, wherein the first exogenous nucleic acid comprises a first selectable marker gene, and the second exogenous nucleic acid comprises a second selectable marker gene, wherein the first and second selectable marker genes are different.

16. The system of the claim 14, wherein
the first vector comprising from 5' to 3', the first RRS, the first nucleic acid comprising the first LCF, and the third RRS; and
the second vector comprising 5' to 3', the third RRS, the second nucleic acid, wherein the second nucleic acid comprising both the nucleotide sequence encoding the first HCF and the nucleotide sequence encoding the second HCF, and the second RRS.

17. The system of the claim 14, wherein
the first vector comprising from 5' to 3', the first RRS, the first nucleic acid comprising the nucleotide sequence encoding the first LCF and the nucleotide sequence encoding the second HCF, and the third RRS; and
the second vector comprising 5' to 3', the third RRS, the second nucleic acid comprising the nucleotide sequence encoding the first HCF, and the second RRS.

18. The system of claim 14, wherein the nucleotide sequence encoding the first HCF encodes a first CH3 domain, and the nucleotide sequence encoding the second HCF encodes a second CH3 domain.

19. The system of claim 18, wherein one of the first and second CH3 domains is the CH3 domain of a human IgG, and the other one is a modified CH3 domain of the human IgG comprising a modification of at least one amino acid position.

20. A method, comprising:
(i) providing the system of claim 14;
(ii) introducing the vectors simultaneously into the cell by transfection; and
(iii) selecting a transfected cell where the first and second nucleic acids in the vectors have integrated into the enhanced expression locus of the cell through recombination mediated by the first, second and third RRSs.

21. The method of claim 20, further comprising:
(iv) expressing the first LCF, the first HCF, and the second HCF in the selected transfected cell; and
(v) obtaining the bispecific antigen-binding protein comprising the first LCF, the first HCF and the second HCF from the selected transfected cell.

22. A method of making a bispecific antigen-binding protein, comprising:
(i) providing the cell of claim 1;
(ii) expressing the bispecific antigen-binding protein from the exogenous nucleic acid sequence; and
(iii) obtaining the bispecific antigen-binding protein from the cell.

23. The cell of claim 1, wherein the nucleotide sequence encoding the first HCF encodes a first CH3 domain, the nucleotide sequence encoding the second HCF encodes a second CH3 domain, wherein the first and second CH3 domains differ in at least one amino acid position.

24. The cell of claim 1, wherein the nucleotide sequence encoding the first HCF encodes a first VH, the nucleotide sequence encoding the second HCF encodes a second VH, and the nucleotide sequence encoding the first LCF encodes a first VL.

25. The cell of claim 1, wherein the cell is a CHO cell.

26. The cell of claim 1, wherein the enhanced expression locus comprises a nucleotide sequence at least 90% identical to SEQ ID NO: 1 or SEQ ID NO: 2.

27. The cell of claim 1, wherein the enhanced expression locus comprises the nucleotide sequence of SEQ ID NO: 1.

28. The cell of claim 1, wherein the enhanced expression locus comprises the nucleotide sequence of SEQ ID NO: 2.

29. The set of vectors of claim 2, wherein the nucleotide sequence encoding the first HCF encodes a first CH3 domain, the nucleotide sequence encoding the second HCF encodes a second CH3 domain, and the first and second CH3 domains differ in at least one amino acid position.

30. The set of vectors of claim 2, wherein the nucleotide sequence encoding the first HCF encodes a first VH, the nucleotide sequence encoding the second HCF encodes a second VH, and the nucleotide sequence encoding the first LCF encodes a first VL.

31. The system of claim 14, wherein the nucleotide sequence encoding the first HCF encodes a first VH, the nucleotide sequence encoding the second HCF encodes a second VH, and the nucleotide sequence encoding the first LCF encodes a first VL.

32. The system of claim 14, wherein the cell is a CHO cell.

33. The system of claim 14, wherein the enhanced expression locus comprises a nucleotide sequence at least 90% identical to SEQ ID NO: 1 or SEQ ID NO: 2.

34. The system of claim 14, wherein the enhanced expression locus comprises the nucleotide sequence of SEQ ID NO: 1.

35. The system of claim 14, wherein the enhanced expression locus comprises the nucleotide sequence of SEQ ID NO: 2.

36. The method of claim 20, wherein the nucleotide sequence encoding the first HCF encodes a first CH3 domain, the nucleotide sequence encoding the second HCF encodes a second CH3 domain, and the first and second CH3 domains differ in at least one amino acid position.

37. The method of claim 20, wherein the nucleotide sequence encoding the first HCF encodes a first VH, the nucleotide sequence encoding the second HCF encodes a second VH, and the nucleotide sequence encoding the first LCF encodes a first VL.

38. The method of claim 20, wherein the cell is a CHO cell.

39. The method of claim 20, wherein the enhanced expression locus comprises a nucleotide sequence at least 90% identical to SEQ ID NO: 1 or SEQ ID NO: 2.

40. The method of claim 20, wherein the enhanced expression locus comprises the nucleotide sequence of SEQ ID NO: 1.

41. The method of claim 20, wherein the enhanced expression locus comprises the nucleotide sequence of SEQ ID NO: 2.

* * * * *